(12) United States Patent
Sarig et al.

(10) Patent No.: US 12,023,348 B2
(45) Date of Patent: Jul. 2, 2024

(54) EGR1 TARGETING MOLECULES FOR THE TREATMENT OF INFLAMMATORY AND HYPERPROLIFERATIVE CONDITIONS

(71) Applicant: The Medical Research, Infrastructure and Health Services Fund of the Tel Aviv Medical Center, Tel-Aviv (IL)

(72) Inventors: Ofer Sarig, Ramat-Yishai (IL); Eli Sprecher, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 15/569,407

(22) PCT Filed: Apr. 26, 2016

(86) PCT No.: PCT/IL2016/050439
§ 371 (c)(1),
(2) Date: Oct. 26, 2017

(87) PCT Pub. No.: WO2016/174674
PCT Pub. Date: Nov. 3, 2016

(65) Prior Publication Data
US 2018/0289728 A1 Oct. 11, 2018

Related U.S. Application Data

(60) Provisional application No. 62/153,087, filed on Apr. 27, 2015.

(51) Int. Cl.
*A61K 31/704* (2006.01)
*A61K 31/122* (2006.01)
(Continued)

(52) U.S. Cl.
CPC .......... *A61K 31/704* (2013.01); *A61K 31/122* (2013.01); *A61K 31/137* (2013.01);
(Continued)

(58) Field of Classification Search
CPC .. A61K 31/704; A61K 31/122; A61K 31/137; A61K 31/16; A61K 31/277;
(Continued)

(56) References Cited

U.S. PATENT DOCUMENTS 3,655,699 A 4/1972 Rutner
5,102,883 A 4/1992 Ackerman et al.
(Continued)

FOREIGN PATENT DOCUMENTS

CN 1414854 4/2003
CN 104224785 12/2014
(Continued)

OTHER PUBLICATIONS

Bhattacharyya et al. PLoS ONE Sep. 1, 2011 vol. 6 Issue 9 e23082 pp. 1-7 (Year: 2011).*

(Continued)

*Primary Examiner* — Jeffrey S Lundgren
*Assistant Examiner* — William Y Lee

(57) ABSTRACT

A method of treating an inflammation or a hyperproliferative disease in a subject in need thereof is disclosed. The method comprising administering to the subject a therapeutically effective amount of a compound selected from the group consisting of:
a compound represented by Formula I:

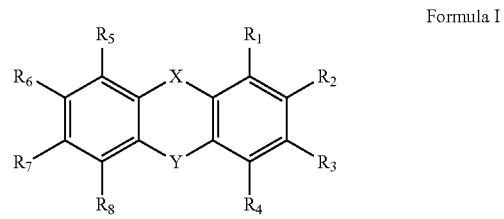

or a pharmaceutically acceptable salt thereof,
a compound represented by Formula II:

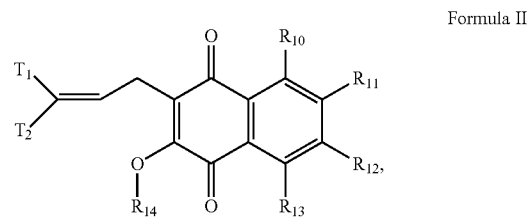

and a compound represented by Formula III:

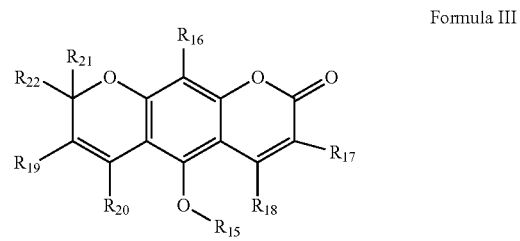

wherein the variables in Formulae I, II and III are as defined in the specification.

11 Claims, 13 Drawing Sheets
(2 of 13 Drawing Sheet(s) Filed in Color)
Specification includes a Sequence Listing.

(51) Int. Cl.

| | | |
|---|---|---|
| *A61K 31/137* | (2006.01) | |
| *A61K 31/167* | (2006.01) | |
| *A61K 31/277* | (2006.01) | |
| *A61K 31/365* | (2006.01) | |
| *A61K 31/366* | (2006.01) | |
| *A61K 31/37* | (2006.01) | |
| *A61K 31/404* | (2006.01) | |
| *A61K 31/423* | (2006.01) | |
| *A61K 31/427* | (2006.01) | |
| *A61K 31/433* | (2006.01) | |
| *A61K 31/4402* | (2006.01) | |
| *A61K 31/4453* | (2006.01) | |
| *A61K 31/4535* | (2006.01) | |
| *A61K 31/454* | (2006.01) | |
| *A61K 31/4738* | (2006.01) | |
| *A61K 31/4741* | (2006.01) | |
| *A61K 31/4745* | (2006.01) | |
| *A61K 31/475* | (2006.01) | |
| *A61K 31/498* | (2006.01) | |
| *A61K 31/53* | (2006.01) | |
| *A61K 31/538* | (2006.01) | |
| *A61K 31/5415* | (2006.01) | |
| *A61K 31/566* | (2006.01) | |
| *A61K 31/58* | (2006.01) | |
| *A61K 31/688* | (2006.01) | |
| *A61K 45/06* | (2006.01) | |
| *A61P 17/00* | (2006.01) | |
| *A61P 17/06* | (2006.01) | |

(52) U.S. Cl.
CPC .......... *A61K 31/167* (2013.01); *A61K 31/277* (2013.01); *A61K 31/365* (2013.01); *A61K 31/366* (2013.01); *A61K 31/37* (2013.01); *A61K 31/404* (2013.01); *A61K 31/423* (2013.01); *A61K 31/427* (2013.01); *A61K 31/433* (2013.01); *A61K 31/4402* (2013.01); *A61K 31/4453* (2013.01); *A61K 31/4535* (2013.01); *A61K 31/454* (2013.01); *A61K 31/4738* (2013.01); *A61K 31/4741* (2013.01); *A61K 31/4745* (2013.01); *A61K 31/475* (2013.01); *A61K 31/498* (2013.01); *A61K 31/53* (2013.01); *A61K 31/538* (2013.01); *A61K 31/5415* (2013.01); *A61K 31/566* (2013.01); *A61K 31/58* (2013.01); *A61K 31/688* (2013.01); *A61K 45/06* (2013.01); *A61P 17/00* (2018.01); *A61P 17/06* (2018.01)

(58) Field of Classification Search
CPC .... A61K 31/365; A61K 31/366; A61K 31/37; A61K 31/404; A61K 31/423; A61K 31/427; A61K 31/433; A61K 31/4402; A61K 31/4453; A61K 31/4535; A61K 31/454; A61K 31/4738; A61K 31/4741; A61K 31/4745; A61K 31/475; A61K 31/498; A61K 31/53; A61K 31/538; A61K 31/5415; A61K 31/566; A61K 31/58; A61K 31/688; A61K 45/06; A61P 17/06; A61P 17/00
See application file for complete search history.

(56) References Cited

U.S. PATENT DOCUMENTS

| | | |
|---|---|---|
| 2004/0010001 A1 | 1/2004 | Au et al. |
| 2004/0063702 A1 | 4/2004 | Koch et al. |
| 2004/0223971 A1 | 11/2004 | Chang et al. |
| 2008/0107720 A1 | 5/2008 | Walters et al. |
| 2009/0214474 A1 | 8/2009 | Jennings |
| 2013/0338207 A1 | 12/2013 | Arbiser |
| 2014/0011812 A1 | 1/2014 | Regev et al. |
| 2015/0056192 A1 | 2/2015 | Chaturvedi et al. |
| 2023/0285383 A1 | 9/2023 | Sprecher |

FOREIGN PATENT DOCUMENTS

| | | |
|---|---|---|
| CN | 109553608 | 4/2019 |
| EP | 0502668 | 9/1992 |
| EP | 502668 | 9/1992 |
| EP | 1491544 | 12/2004 |
| KR | 2011-010609 | 2/2011 |
| WO | WO 2004/085418 | 10/2004 |
| WO | WO 2005/007129 | 1/2005 |
| WO | WO 2006/002082 | 1/2006 |
| WO | WO 2006/094207 | 9/2006 |
| WO | WO 2007/092436 | 8/2007 |
| WO | WO 2008/016661 | 2/2008 |
| WO | WO 2009/017795 | 2/2009 |
| WO | WO 2014/011540 | 1/2014 |
| WO | WO 2014/153241 | 9/2014 |
| WO | WO 2014/179528 | 11/2014 |
| WO | WO 2015/153535 | 10/2015 |
| WO | WO 2016/174674 | 11/2016 |
| WO | WO 2014/011540 | 4/2020 |
| WO | WO 2022/074649 | 4/2022 |

OTHER PUBLICATIONS

International Search Report and the Written Opinion Dated Sep. 23, 2016 From the International Searching Authority Re. Application No. PCT/IL2016/050439.

Cermak et al. "The Transcription Factor EGR1 Regulates Metastatic Potential of V-SRC Transformed Sarcoma Cells", Cellular and Molecular Life Sciences, 67: 3557-3568, Published Online May 28, 2010.

Chan et al. "Anti-Inflammatory Principles From the Stem and Root Barks of Citrus Medica", Chemical and Pharmaceutical Bulletin, XP002761662, 58(1): 61-65, Published Online Oct. 29, 2010. p. 63, Table 2.

Chefetz et al. "Normophosphatemic Familial Tumoral Calcinosis is Caused by Deleterious Mutations in SAMD9, Encoding a TNF-Alpha Responsive Protein", Journal of Investigative Dermatology, 128: 1423-1429, Published Online Dec. 20, 2007.

Hershkovitz et al. "Functional Characterization of SAMD9, a Protein Deficient in Normophosphatemic Familial Tumoral Calcinosis", Journal of Investigative Dermatology, 131: 662-669, Published Online Dec. 16, 2010.

Kawaii et al. "Antiproliferative Effect of Isopentenylated Coumarins on Several Cancer Cell Lines", Anticancer Research, XP002979341, 21(38): 1905-1911, Jan. 1, 2001. p. 1907, Compounds 22-25, p. 1909, Fig.2.

Molloy et al. "Basic Calcium Phosphate Crystals: Pathways to Joint Degeneration", Current Opinion in Rheumatology, 18: 187-192, 2006.

Nakamura et al. "Inhibitory Effect of Oxycoumarins Isolated From the Thai Medicinal Plant Clausena Guillauminii on the Inflammation Mediators, iNOS, TNF-Alpha, and COX-2 Expression in Mouse Macrophage RAW 264.7", Journal of Nature Medicine, , XP002761663, 63: 21-27, Published Online Jul. 19, 2008. p. 24, Fig.1, p. 26, Figs.3-5.

Su et al. "Anti-HBV and Cytotoxic Activities of Pyranocoumarin Derivatives", Bioorganic & Medicinal Chemistry, XP002761664, 17: 6137-6143, Available Online Dec. 13, 2008. p. 6140, Table 2, Compounds 2, 3, 5, 8, 10-12, 15, 18.

International Preliminary Report on Patentability Dated Nov. 9, 2017 From the International Bureau of WIPO Re. Application No. PCT/IL2016/050439. (10 Pages).

Communication Pursuant to Article 94(3) EPC Dated Sep. 25, 2019 From the European Patent Office Re. Application No. 16722951.7. (7 Pages).

(56) References Cited

OTHER PUBLICATIONS

Office Action Dated Oct. 22, 2019 From the Israel Patent Office Re. Application No. 255290 and Its Translation Into English. (11 Pages).
Notification of Office Action Dated Feb. 5, 2021 From the State Intellectual Property Office of the People's Republic of China Re. Application No. 201680037911.9 and Its Translation Into English. (5 Pages).
Li et al. "Camptothecin (CPT) and Its Derivatives Are Known to Target Topoisomerase I (Top1) as Their Mechanism of Action: Did We Miss Something in CPT Analogue Molecular Targets for Treating Human Disease Such as Cancer?", American Journal of Cancer Research, 7(12): 2350-2394, Dec. 1, 2017.
Office Action Dated Nov. 11, 2020 From the Israel Patent Office Re. Application No. 255290 and Its Translation Into English. (6 Pages).
Communication Pursuant to Article 94(3) EPC Dated Apr. 30, 2020 From the European Patent Office Re. Application No. 16722951.7. (4 Pages).
Notification of Office Action and Search Report Dated Apr. 23, 2020 From the National Intellectual Property Administration of the People's Republic of China Re. Application No. 201680037911.9 and Its Translation Into English. (26 Pages).
Examination Report Dated Sep. 18, 2020 From the Australian Government, IP Australia Re. Application No. 2016255725. (15 Pages).
Notification of Office Action and Search Report Dated Sep. 14, 2020 From the National Intellectual Property Administration of the People's Republic of China Re. Application No. 201680037911.9 and Its Translation Into English. (17 Pages).
Patent Examination Report Dated Aug. 20, 2021 From the Australian Government, IP Australia Re. Application No. 2016255725. (3 Pages).
Communication Pursuant to Article 94(3) EPC Dated Oct. 19, 2021 From the European Patent Office Re. Application No. 16722951.7. (5 Pages).
Office Action Dated Oct. 31, 2021 From the Israel Patent Office Re. Application No. 255290 and Its Translation Into English. (6 Pages).
International Search Report and the Written Opinion Dated Jan. 4, 2022 From the International Searching Authority Re. Application No. PCT/IL2021/051197 (16 Pages).

Chiao et al. "Effect of Topical Use of Camptothecine-Dimethyl Sulfoxide Solution in Psoriasis", Chinese Medical Journal, 1(05): 355-360, Sep. 1975.
Daud et al. "Phase II Trial of Karenitecin in Patients with Malignant Melanoma: Clinical and Translational Study", Clinical Cancer Research, 11(8): 3009-3016, Apr. 15, 2005.
Galatage et al. "Design and characterization of Camptothecin Gel for Treatment of Epidermoid Carcinoma", Future Journal of Pharmaceutical Sciences, 6(1): 1-11, Aug. 5, 2020.
Lin et al. "Clinical Trial and Experimental Study on Treating Psoriasis with Camptothecine", Chinese Medical Journal, 101(06): 427-30, Published Online 1988.
Lin et al. "Topical Camptothecine in Treatment of Psoriasis", International Journal of Dermatology, 27(7): 475-477, Sep. 1988.
O'Reilly et al. "The Clinical Status of Irinotecan (CPT-11), a Novel Water Soluble Camptothecin Analogue: 1996", Critical Reviews in Oncology/ Hematology, 24(1): 47-70, Available online Mar. 12, 1999.
Rossi et al. "Identification of Early Gene Expression Changes in Primary Cultured Neurons Treated with Topoisomerase I Poisons", Biochemical and Biophysical Research Communications, 479(2): 319-324, Available online Sep. 15, 2016.
Sun et al. "A Comparison of the Effects of Topical Treatment of Calcipotriol, Camptothecin, Clobetasol and Tazarotene on an Imiquimod-Induced Psoriasis-Like Mouse Model", Immunopharmacology and Immunotoxicology, 36(1): 17-24, Published online Nov. 29, 2013.
Sun et al. "Camptothecin Fails to Induce Apoptosis in Tumor Necrosis Factor-Alpha-Treated HaCaT Cells", Pharmacology, 89(1-2): 58-63, Published online Feb. 1, 2012.
Venancio et al. "Topotecan-Loaded Lipid Nanoparticles as a Viable Tool for the Topical Treatment of Skin Cancers", Journal of Pharmacy and Pharmacology, 69(10): 1318-1326, Jul. 13, 2017.
Requisition by the Examiner Dated Jun. 13, 2022 From the Innovation, Science and Economic Development Canada, Canadian Intellectual Property Office Re. Application No. 2,986,202. (4 Pages).
Office Action Dated Jan. 2, 2023 From the Israel Patent Office Re. Application No. 255290 and Its Translation Into English. (6 Pages).
International Preliminary Report on Patentability Apr. 20, 2023 From the International Bureau of WIPO Re. Application No. PCT IL2021/051197. (9 Pages).

* cited by examiner

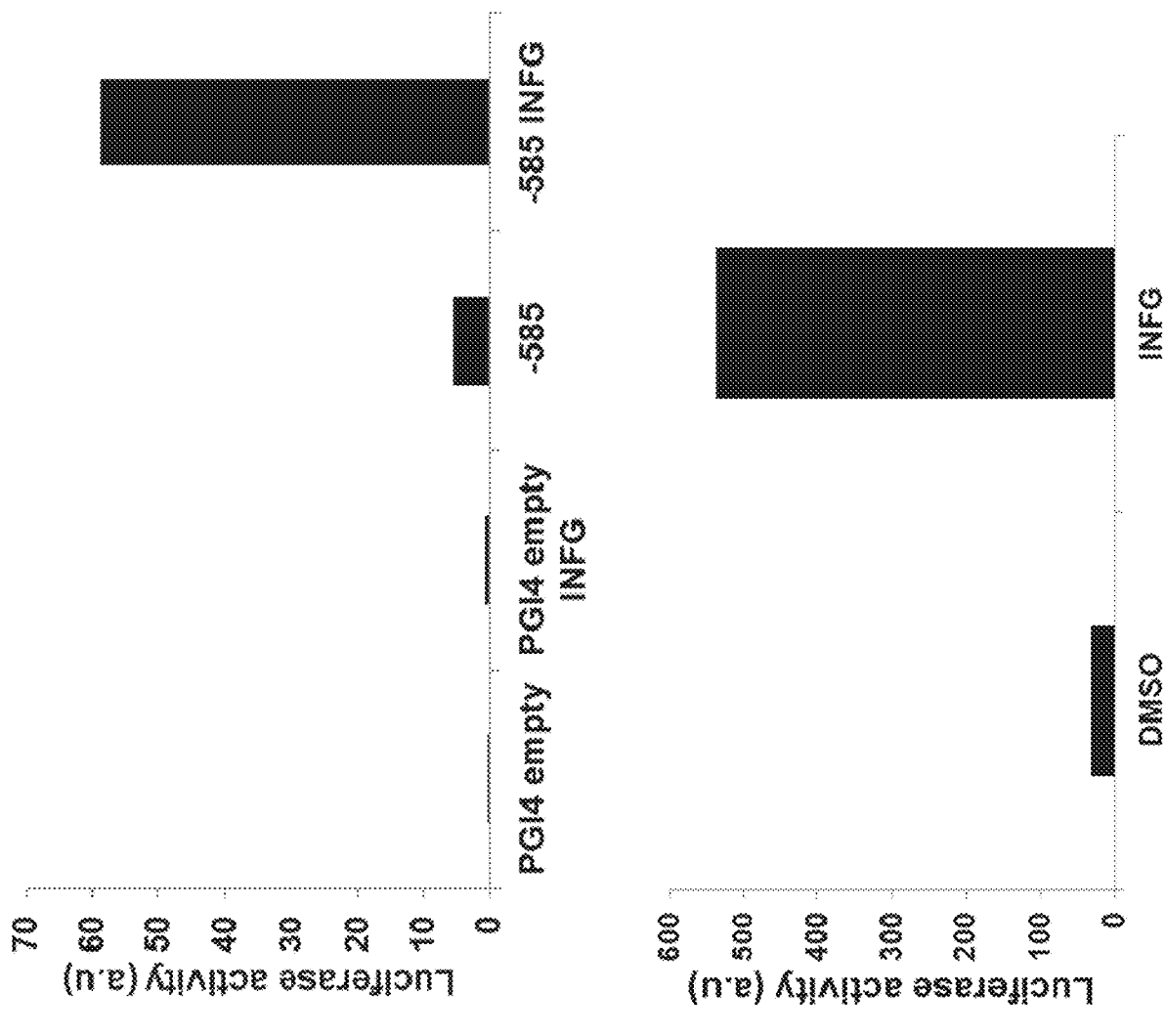

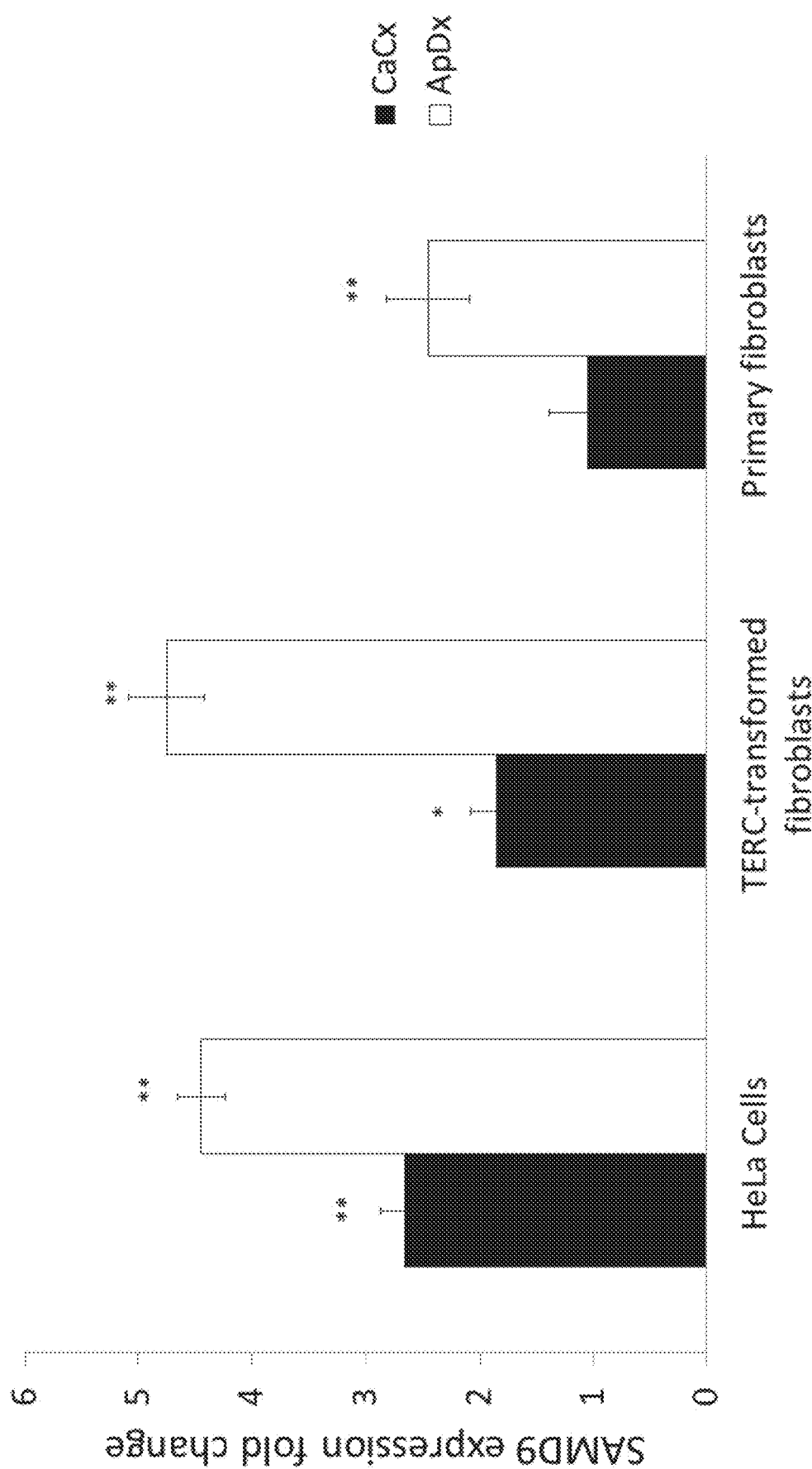

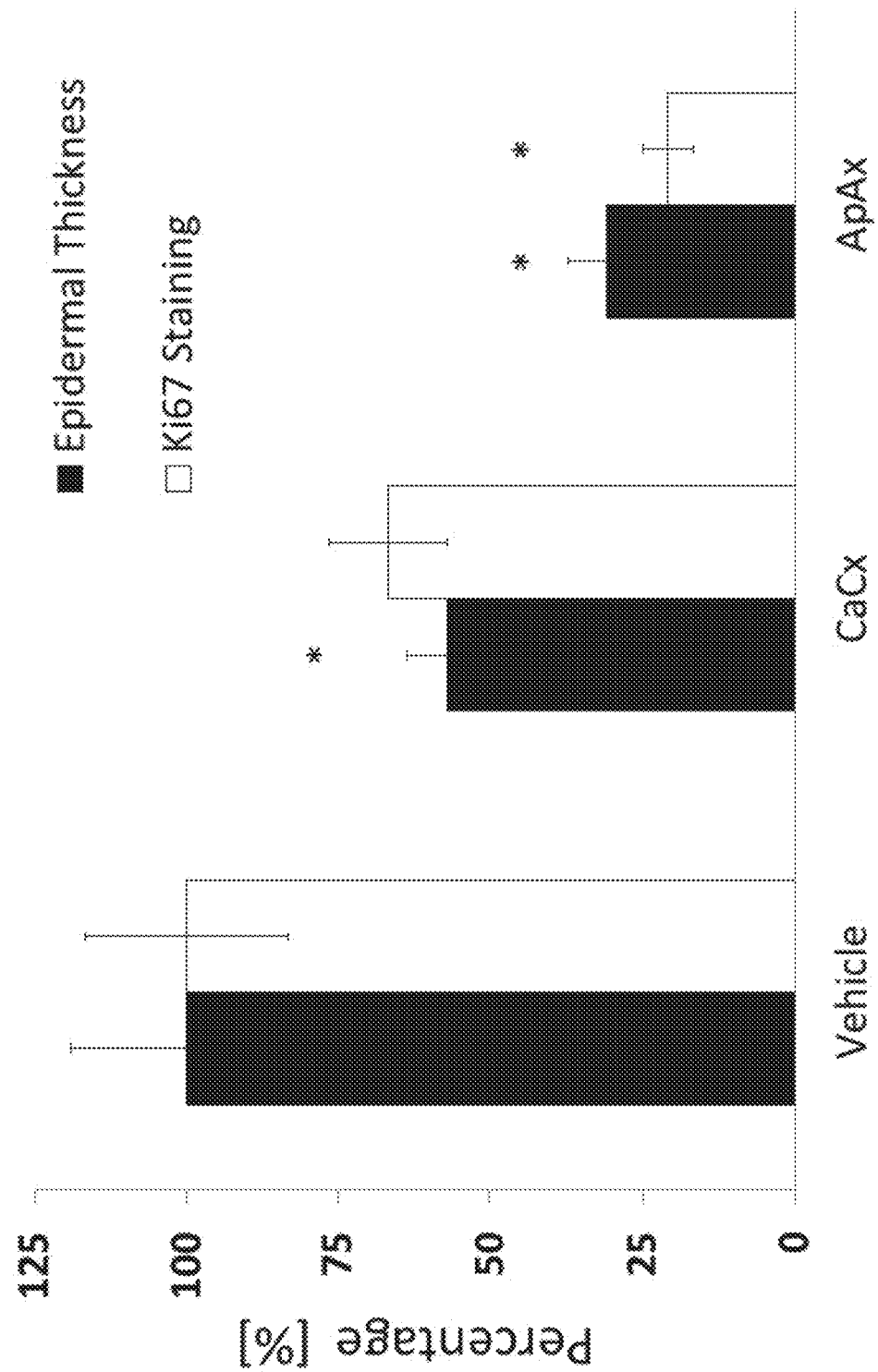

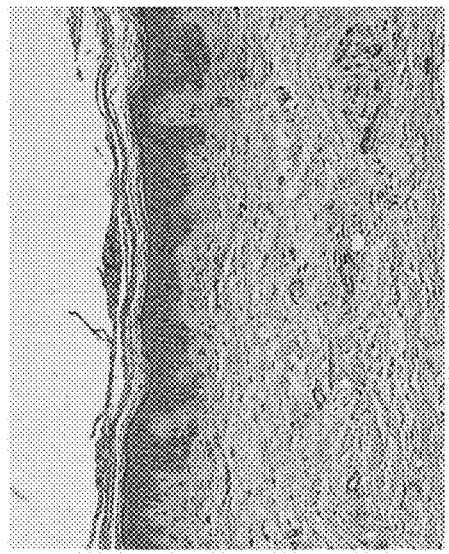
FIG. 7C ApDx
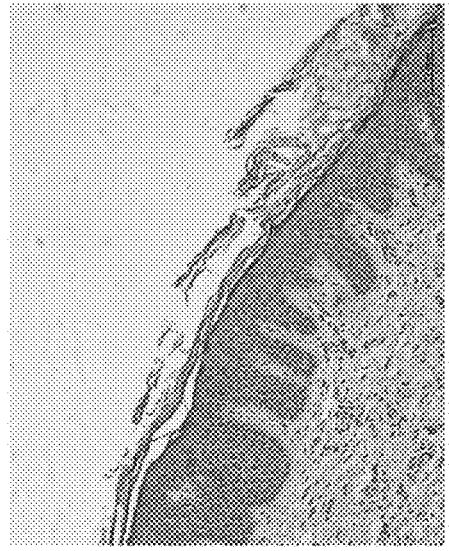
FIG. 7B CaCx
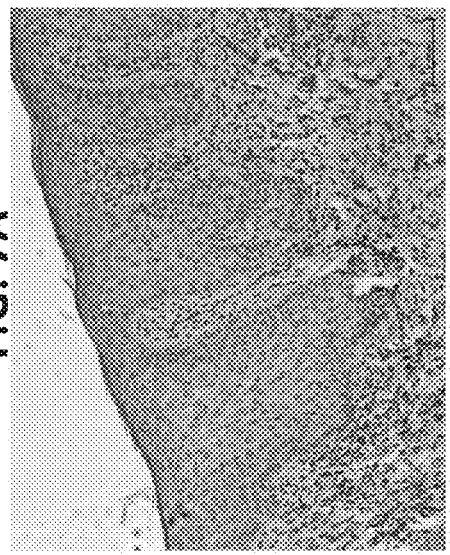
FIG. 7A Vehicle
H&E
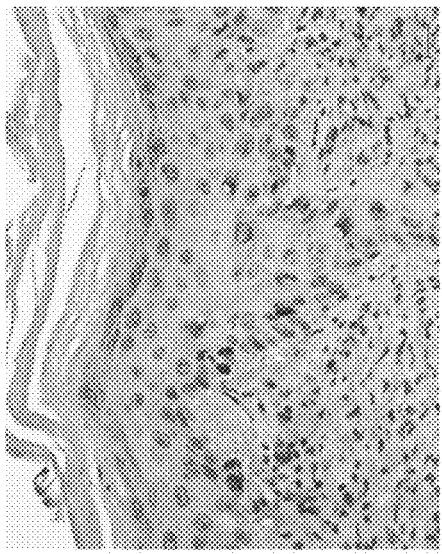
FIG. 7F
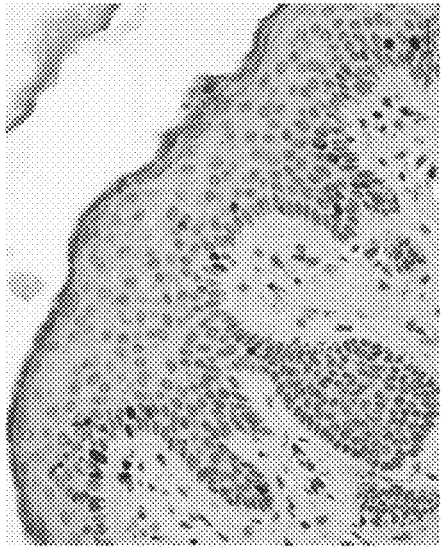
FIG. 7E
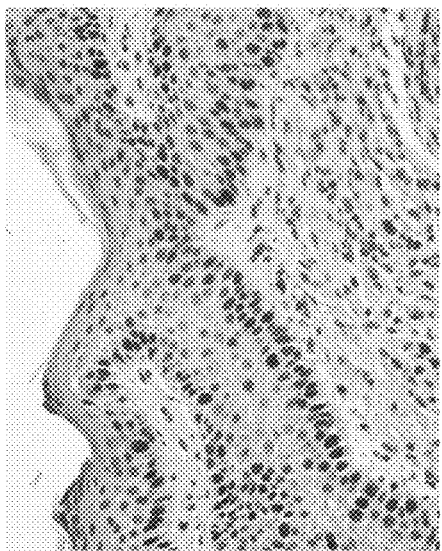
FIG. 7D
Ki67

EGR1 TARGETING MOLECULES FOR THE TREATMENT OF INFLAMMATORY AND HYPERPROLIFERATIVE CONDITIONS

RELATED APPLICATIONS

This application is a National Phase of PCT Patent Application No. PCT/IL2016/050439 having International filing date of Apr. 26, 2016, which claims the benefit of priority under 35 USC § 119(e) of U.S. Provisional Patent Application No. 62/153,087 filed on Apr. 27, 2015. The contents of the above applications are all incorporated by reference as if fully set forth herein in their entirety.

SEQUENCE LISTING STATEMENT

The ASCII file, entitled 71489SequenceListing.txt, created on Oct. 26, 2017, comprising 2,209 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to therapy and, more particularly, but not exclusively, to EGR1 targeting drugs and to use thereof for the treatment of inflammatory and hyperproliferative conditions.

The study of rare monogenic disorders often reveals hitherto unknown biological pathways.

Familial tumoral calcinosis (FTC) represents a clinically and genetically heterogeneous group of inherited diseases manifesting with dermal and subcutaneous deposition of calcified materials. It was previously demonstrated that the normophosphatemic variant of FTC (NFTC) is caused by mutations in the sterile alpha motif domain 9 (SAMD9) gene which encodes a 170 kD protein [Chefetz, I. et al. (2008) *J Invest Dermatol* 128: 1423-9]. NFTC is inherited in an autosomal recessive manner, and has been exclusively reported in Yemenite Jews. Several inflammatory cytokines, including tumor necrosis factor alpha (TNF-α) and interferon-gamma (IFN-γ), regulate SAMD9 gene expression [Chefetz, I. et al. (2008), supra], which may explain the fact that in NFTC, inflammation seems to precede ectopic calcification in the skin.

It was previously established that SAMD9 may function by inhibiting EGR1 (Early growth response protein 1) expression [Hershkovitz, D. et al. (2011) *J Invest Dermatol* 131: 662-9]. The EGR1 gene product is a transcription factor with roles in differentiation and growth. EGR1 is also an important mediator of inflammation and may be involved in the pathogenesis of Crohn's disease, where SAMD9 is down-regulated, and scleroderma, a disorder notoriously featuring ectopic calcification. Moreover, tissue deposition of calcium phosphate has been associated with increased EGR1 expression [Molloy, E. S. and McCarthy, G. M. (2006) *Curr Opin Rheumatol* 18: 187-92]. EGR1 has also been implicated in the pathogenesis of breast, prostate, and lung cancer and may be important for metastatic progression due to the activation of genes that control actin contractility [Cermak, V. et al. (2010) *Cell Mol Life Sci* 67: 3557-68], an observation that is in line with data showing intracellular redistribution of actin filaments following downregulation of SAMD9 [Hershkovitz, D. et al. (2011), supra].

U.S. Patent Application having Publication No. 20140011812 discloses methods of decreasing inflammation by inhibiting polo-like kinase (PlK), and mentions EGR1 as a transcriptional regulator whose expression is associated with the immune response.

Additional background art includes WO 2014/011540 and EP Patent No. 0502668.

SUMMARY OF THE INVENTION

According to an aspect of some embodiments of the present invention there is provided method of treating an inflammation or a hyperproliferative disease in a subject in need thereof, the method comprising administering to the subject a therapeutically effective amount of a compound selected from the group consisting of:

a compound represented by Formula I:

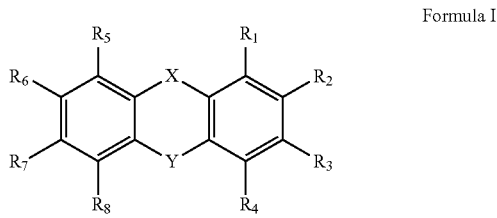

Formula I or a pharmaceutically acceptable salt thereof, wherein:

X is N—$R_9$;

Y is selected from $S(=O)_2$, $C=O$, or is absent;

$R_1$-$R_8$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively or in addition, two of $R_1$-$R_4$ and $R_9$ and/or $R_5$-$R_9$ form together a cyclic ring, the cyclic ring being selected from aryl, heteroaryl, cycloalkyl or heteroalicyclic, a compound represented by Formula II:

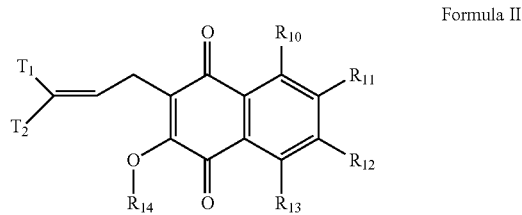

Formula II wherein:

$R_{10}$-$R_{13}$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively, two of $R_{10}$-$R_{13}$ form together a cyclic ring, the cyclic ring being selected from aryl, heteroaryl, cycloalkyl or heteroalicyclic;

$R_{14}$ is hydrogen, alkyl or cycloalkyl; and $T_1$ and $T_2$ are each halo, and a compound represented by Formula III:

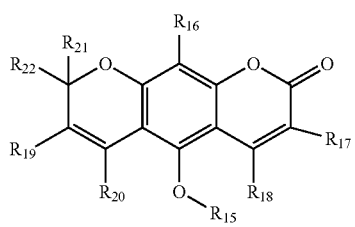

Formula III wherein:

$R_{15}$ is hydrogen, alkyl or cycloalkyl;

$R_{16}$-$R_{22}$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively, two of $R_{15}$, $R_{17}$ and $R_{18}$ and/or two of $R_{15}$ and $R_{19}$-$R_{22}$ form together a cyclic ring, the cyclic ring being selected from aryl, heteroaryl, cycloalkyl and heteroalicyclic, thereby treating the inflammation or the hyperproliferative disease in the subject.

According to an aspect of some embodiments of the present invention there is provided a use of a compound selected from the group consisting of a compound represented by Formula I, Formula II and Formula III, as described herein, in the manufacture of a medicament identified for treating an inflammation or a hyperproliferative disease in a subject in need thereof.

According to an aspect of some embodiments of the present invention there is provided a compound selected from the group consisting of a compound represented by Formula I, Formula II and Formula III, as described herein, for use in the treatment of an inflammation or a hyperproliferative disease in a subject in need thereof.

According to some embodiments of the invention, the inflammation is associated with a chronic inflammatory disease.

According to some embodiments of the invention, the inflammation is associated with an acute inflammatory disease.

According to some embodiments of the invention, the inflammation is associated with a disease selected from the group consisting of an infectious disease, an autoimmune disease, a hypersensitivity associated inflammation, a graft rejection and an injury.

According to some embodiments of the invention, the autoimmune disease is selected from the group consisting of Crohn's disease, psoriasis, scleroderma and rheumatoid arthritis.

According to some embodiments of the invention, the inflammation comprises a skin inflammation.

According to some embodiments of the invention, the skin inflammation is selected from the group consisting of an atopic dermatitis, a contact dermatitis, a dermatitis herpetiformis, a generalized exfoliative dermatitis, a seborrheic dermatitis, a psoriasis, a drug rash, an erythema multiforme, an erythema nodosum, a granuloma annulare, a poison ivy, a poison oak, a toxic epidermal necrolysis, an acne and a rosacea.

According to some embodiments of the invention, the hyperproliferative disease is a cancer or a cancer metastasis.

According to some embodiments of the invention, the cancer is selected from the group consisting of a breast cancer, a prostate cancer, a lung cancer, a neuroblastoma, a melanoma, a colon cancer and a pancreatic cancer.

According to some embodiments of the invention, the hyperproliferative disease is a calcified cancer.

According to some embodiments of the invention, the calcified cancer is a normophosphatemic variant of FTC (NFTC).

According to an aspect of some embodiments of the present invention there is provided an article of manufacture comprising a compound selected from the group consisting of a compound represented by Formula I, Formula II and Formula III, and a chemotherapy, being packaged in a packaging material and identified in print, in or on the packaging material, for use in the treatment of a cancer.

According to an aspect of some embodiments of the present invention there is provided an article of manufacture comprising a compound selected from the group consisting of a compound represented by Formula I, Formula II and Formula III, as described herein, and an anti-inflammatory agent, being packaged in a packaging material and identified in print, in or on the packaging material, for use in the treatment of an inflammation.

According to some embodiments of the invention, the compound represented by Formula I, II or III and the chemotherapy are in separate containers.

According to some embodiments of the invention, the compound represented by Formula I, II or III and the anti-inflammatory agent are in separate containers.

According to some embodiments of the invention, the compound represented by Formula I, II or III and the chemotherapy are in a co-formulation.

According to some embodiments of the invention, the compound represented by Formula I, II or III and the anti-inflammatory agent are in a co-formulation.

According to some of any of the embodiments described herein, the compound is represented by Formula I.

According to some of any of the embodiments described herein, the compound is 7,9-dichloro-5,5-dioxo-10-propylphenothiazin-3-amine.

According to some of any of the embodiments described herein, the compound is 6H-Pyrido[4,3-b]carbazole-1-carboxamide, 5,11-dimethyl-monohydrochloride.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B illustrate SAMD9 promoter activity in transfected HeLa cells. FIG. 1A shows HeLa cells which were transiently transfected with an expression vector pGL4.17 alone (PGL4 empty) or pGL4.17 containing a SAMD9 promoter fragment spanning 585 bp upstream to the TSS and a pRL Renilla luciferase vector. Twenty four hours post-transfection, 10 ng/ml IFN-γ were added. The luciferase data obtained at 48 hours post-transfection were normalized against Renilla; FIG. 1B shows a HeLa cell line stably expressing the expression vector pGL4.17 containing the 585 bp SAMD9 promoter fragment which were cultured in the presence of 10 ng/ml IFN-γ added for 24 hours. Luciferase data were then normalized against Renilla.

FIG. 1C illustrates induction of SAMD9 expression in HeLa Cells, TERC-transformed fibroblasts and primary fibroblasts treated with CaCx and ApDx. All three cell types were cultured in 12-well plates and treated with 5 μM of CaCx (black columns) and ApDx (empty columns) for 24 hours in duplicates. SAMD9 expression was measured via qRT-PCR, in triplicates. Results are expressed as fold-change in SAMD9 RNA expression relative to control cells treated with DMSO±standard error. *=$p<0.05$; **=$p<0.01$.

Figure 2A:
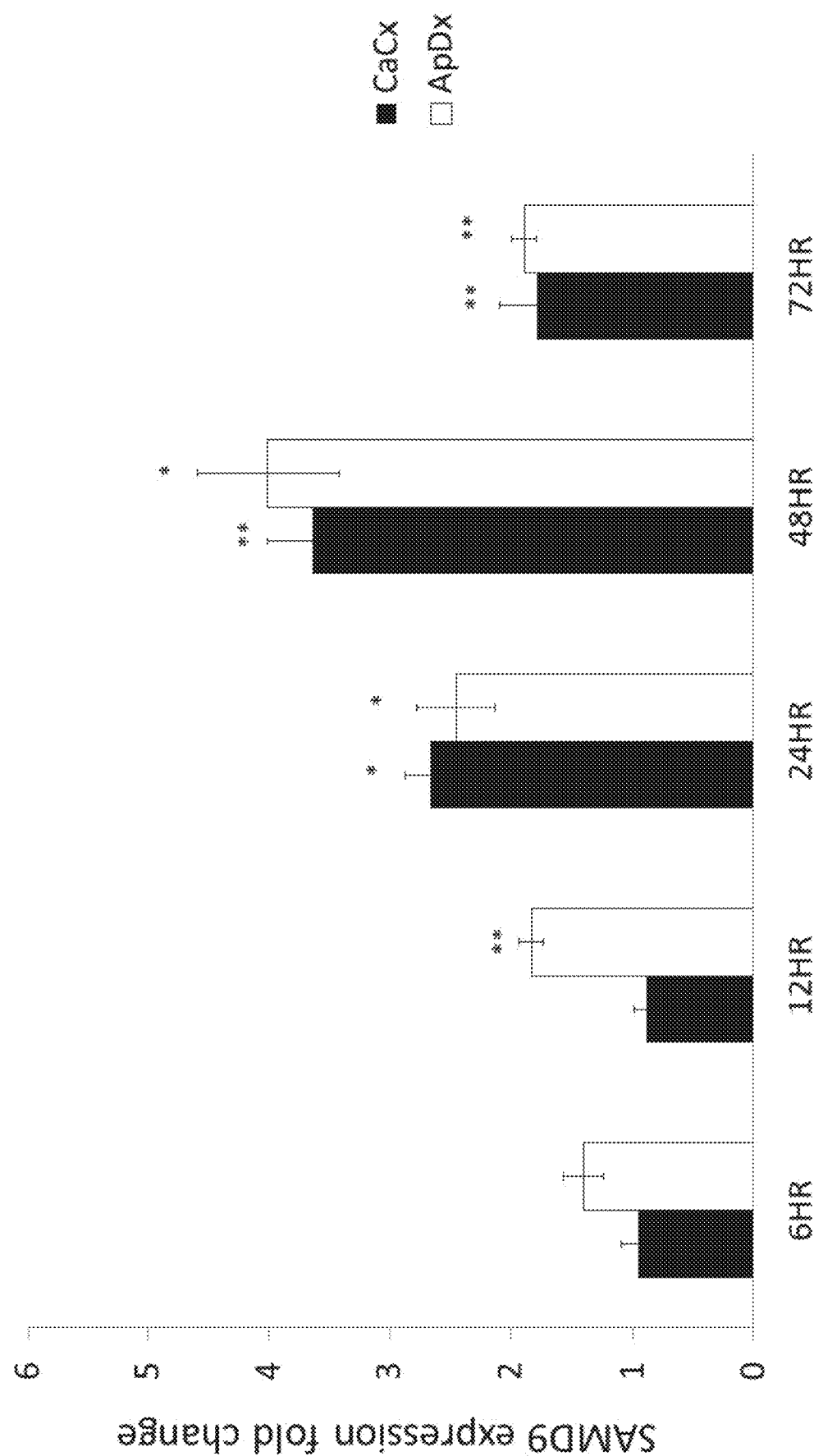
Figure 2B:
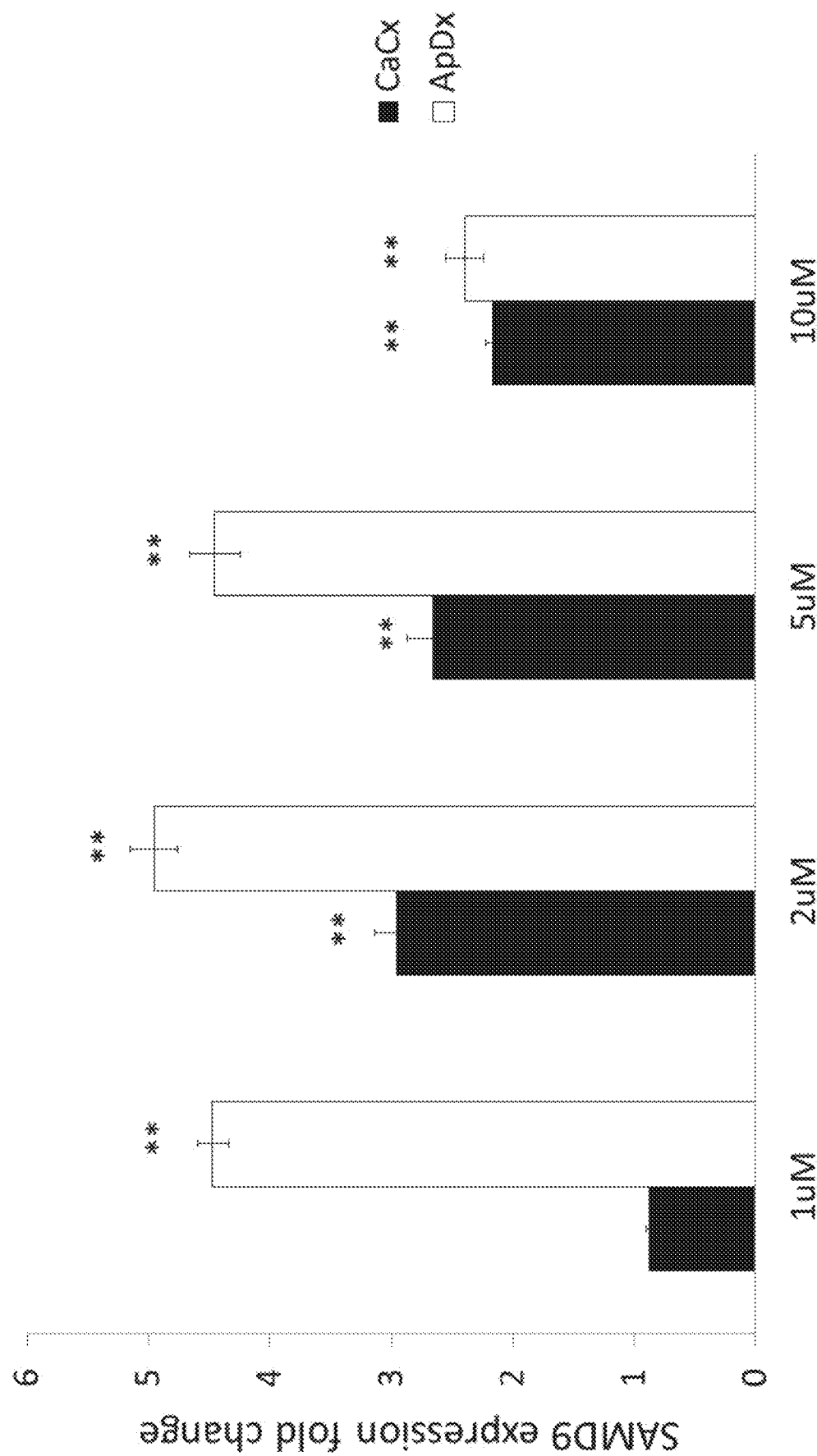

FIGS. 2A-B illustrate induction of SAMD9 expression in primary fibroblasts treated with CaCx and ApDx. Primary fibroblasts were cultured in duplicates in 12-well plates in the presence of 5 μM of CaCx and ApDx (empty columns), or DMSO for 72 hours (FIG. 2A) or in the presence of DMSO or 1 μM, 2 μM, 5 μM and 10 μM CaCx or ApDx, respectively (FIG. 2B). SAMD9 expression was measured via qRT-PCR, all samples were run in triplicates. Results are expressed as SAMD9 RNA expression relative to control primary fibroblasts treated with DMSO±standard error. *=$p<0.05$; **=$p<0.01$.

Figure 3:
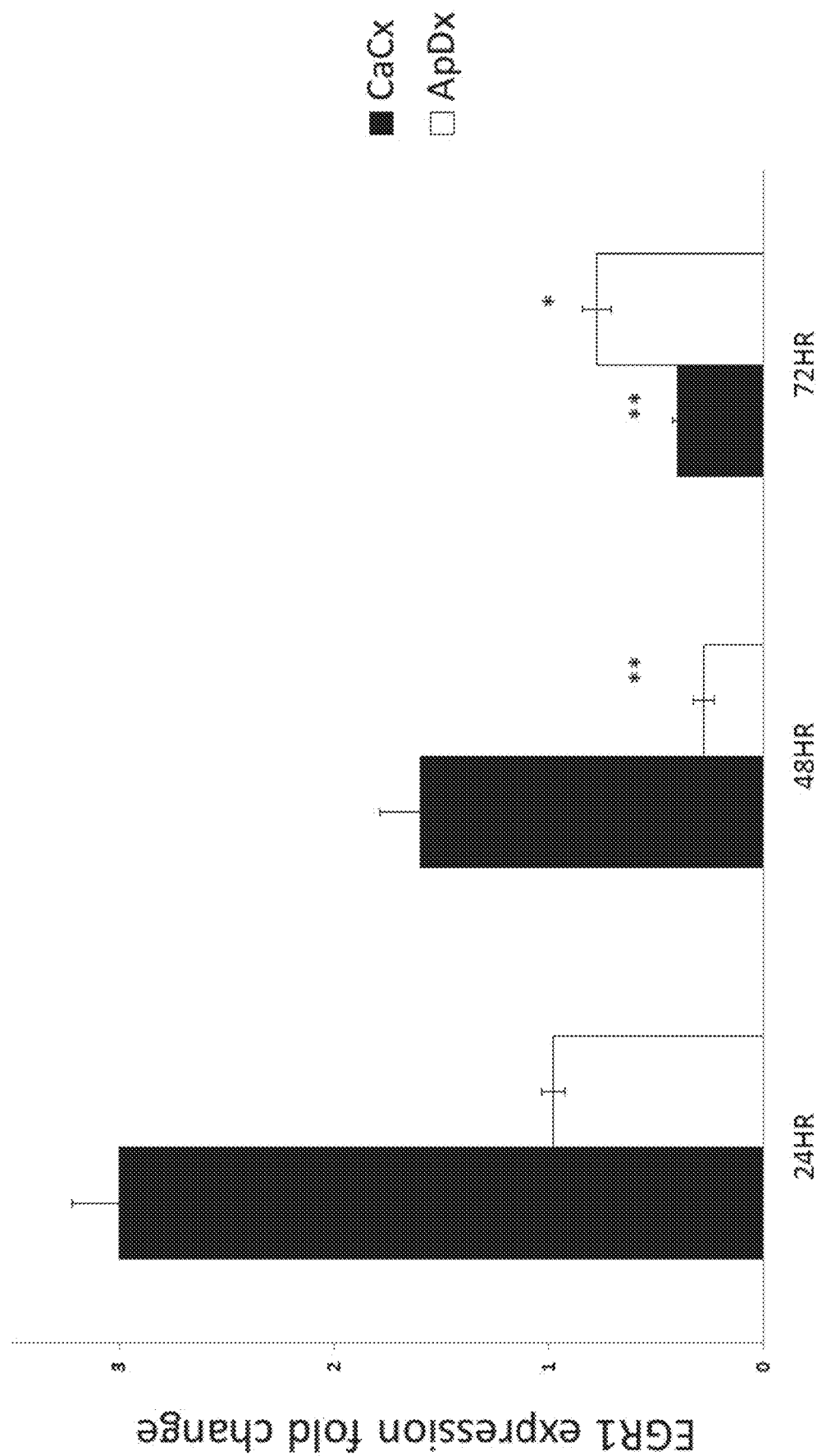

FIG. 3 illustrates CaCx and ApDx effect on EGR1 expression in primary fibroblasts. Primary fibroblasts were cultured in duplicates in 12-well plates over a period of 72 hours in the presence of DMSO, 5 μM of CaCx (black columns) or ApDx (empty columns). Results are expressed as EGR1 RNA expression relative to DMSO treated control±standard error, respectively. *=$p<0.05$; **=$p<0.01$.

Figure 4C:
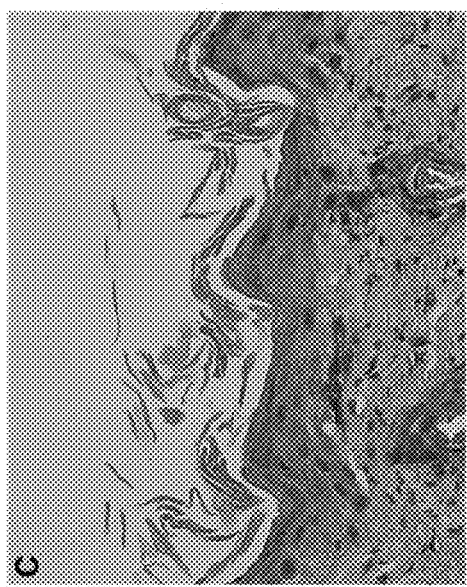
Figure 4F:
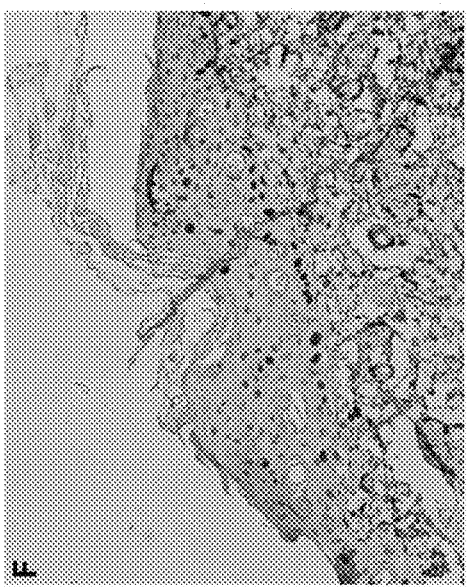
Figure 4B:
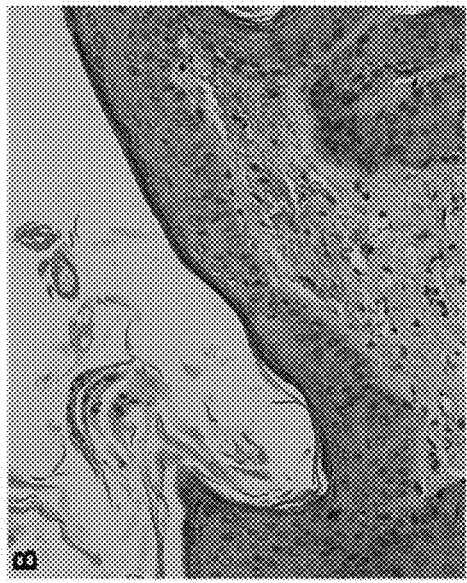
Figure 4E:
Figure 4A:
Figure 4D:

FIGS. 4A-F illustrate a histopathological analysis of the effect of CaCx and ApDx on imiquimod-induced psoriasiform dermatitis in mice. Three groups of mice were treated as follows: group 1 was treated 5 times weekly topically with imiquimod and received i.p. injection of DMSO (FIGS. 4A and 4D); group 2 was treated 5 times weekly topically with imiquimod and receives i.p. injection of CaCx (FIGS. 4B and 4E); group 3 was treated 5 times weekly topically with imiquimod and receives i.p. injection of ApDx (FIGS. 4C and 4F). Biopsies were obtained on day 6 and stained with H&E (upper panels) and Ki67 (lower panels).

Figure 5B:
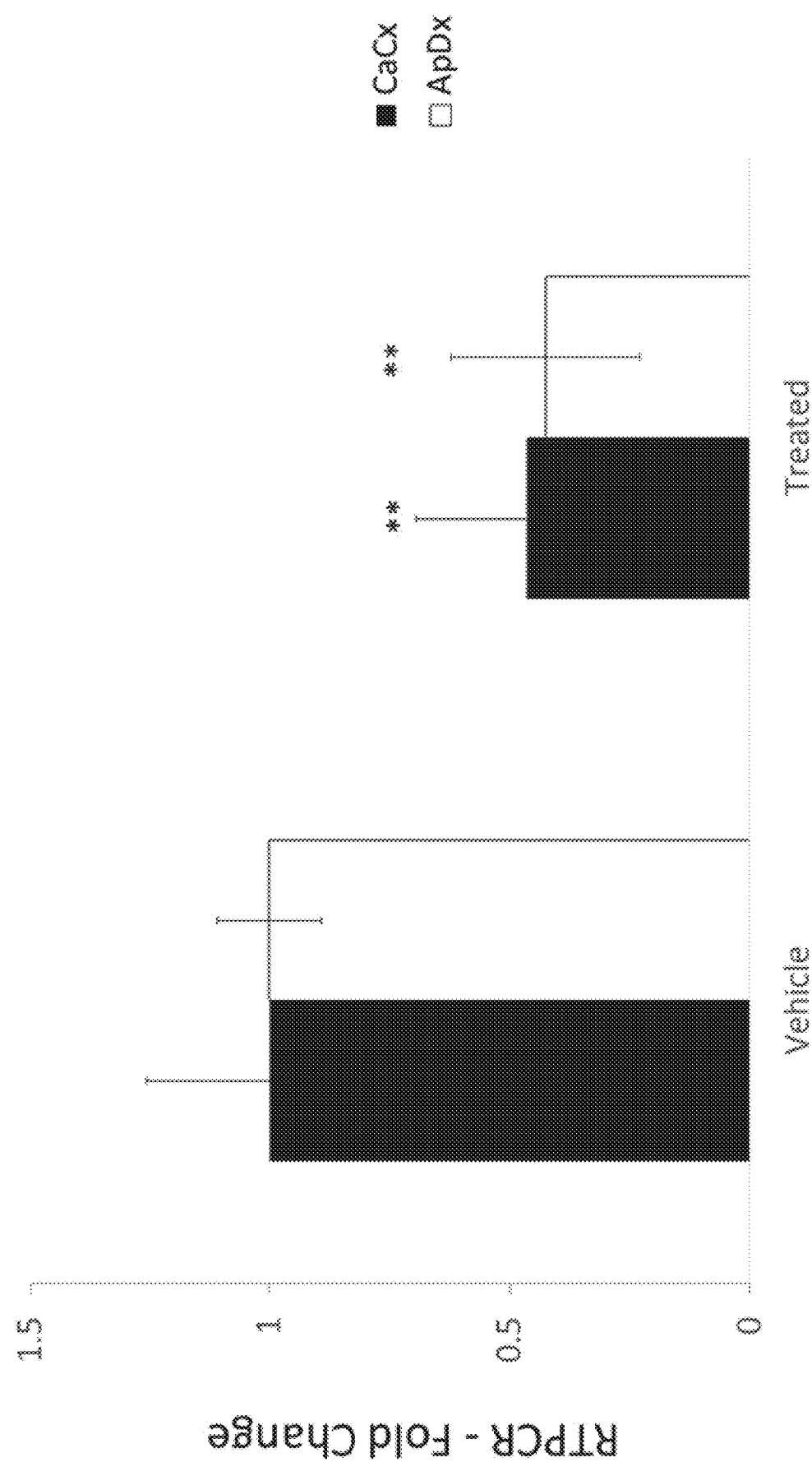
Figure 5C:
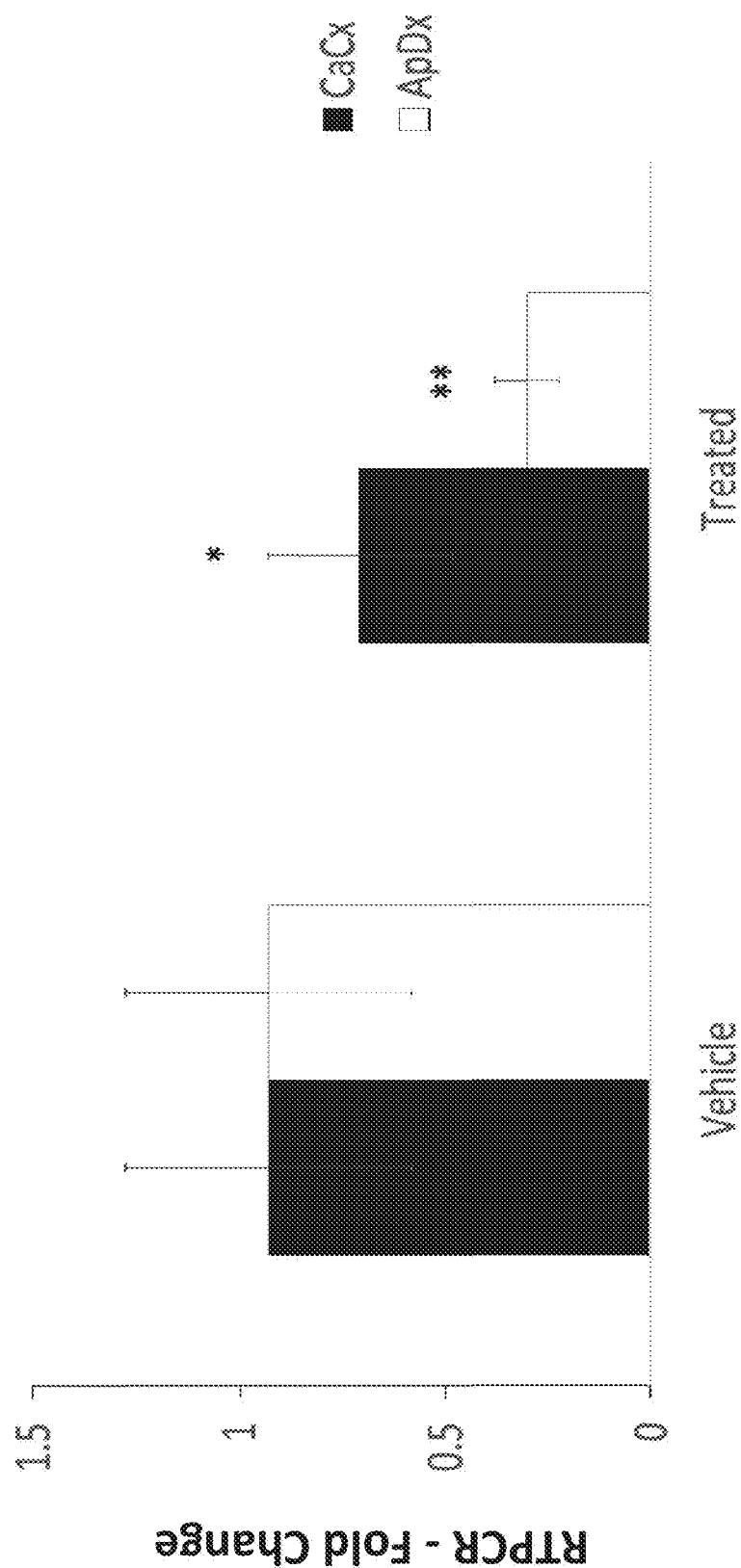

FIGS. 5A-C illustrate Ki67 staining and epidermal thickness after treatment with CaCx and ApDx of imiquimod-induced psoriasiform dermatitis. Twelve Balb/c mice were treated with imiquimod 5% topically daily for 5 days and divided into three equal groups which received concomitantly for 5 days i.p. vehicle (DMSO and lipofuscin 10%); 22.5 mg/kg/day CaCx or 7.5 mg/kg/day ApDx. FIG. 5A shows the epidermal thickness measured in micrometers (black columns) and the percentage of positive Ki67 in the epidermis (white columns); FIGS. 5B-C, in parallel, EGR1 RNA levels (FIG. 5B) and IL-33 RNA levels (FIG. 5C) were measured in triplicates by qRT-PCR. CaCx (black columns) and ApDx (white columns). Results are expressed as EGR1 RNA expression relative to control mice treated with the vehicle treated group±standard error. *=$p<0.05$; **=$p<0.01$.

Figure 6:
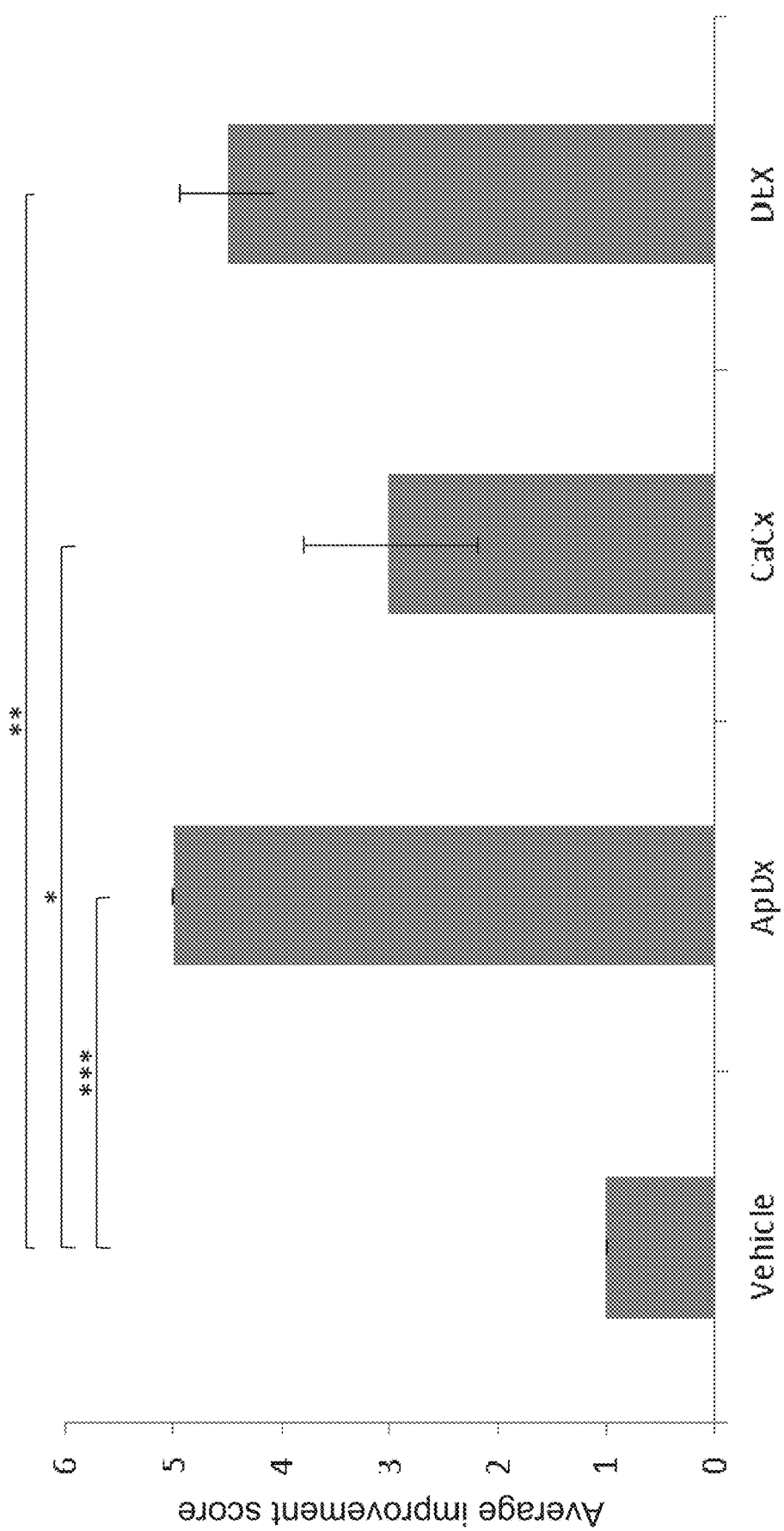

FIG. 6 illustrates CaCx and ApDx effect in chimeric mice carrying human psoriatic skin. Six weeks after human skin grafting, chimeric mice were treated. Four groups of mice were treated as follows: one group of mice was injected i.p. five times a week with the vehicle; a second group of mice was injected five times a week ApDx (5 mg/kg); a third group of mice was injected five times a week CaCx (15 mg/kg); and a fourth group of mice, was treated with dexamethasone (DEX) cream applied 5 times a week on the graft, as positive control (DEX was expected to attenuate inflammation in this model). Each group included five mice, and the treatment was performed for a total of 10 days. The grafts were harvested from the four groups of mice, paraffin-embedded, stained for hematoxylin and eosin (H&E), analyzed and scored for the average improvement of the clinical and histological psoriasiform phenotype. Results represent the average improvement score for each mice group±SE (*$p<0.05$;  $p<0.001$, * $p<0.0001$).

FIGS. 7A-F illustrate a histopathological analysis of the effect of CaCx and ApDx in chimeric mice carrying human psoriatic skin. Three groups of mice were treated as follows: one group of mice was injected i.p. five times a week with the vehicle (FIGS. 7A and 7D); a second group of mice was injected five times a week ApDx (5 mg/kg) (FIGS. 7C and 7F); a third group of mice was injected five times a week CaCx (15 mg/kg) (FIGS. 7B and 7E). Each group included five mice, and the treatment was performed for a total of 10 days. Biopsies were obtained on day 10 and stained with H&E (upper panels) and Ki67 (lower panels).

Figure 8:
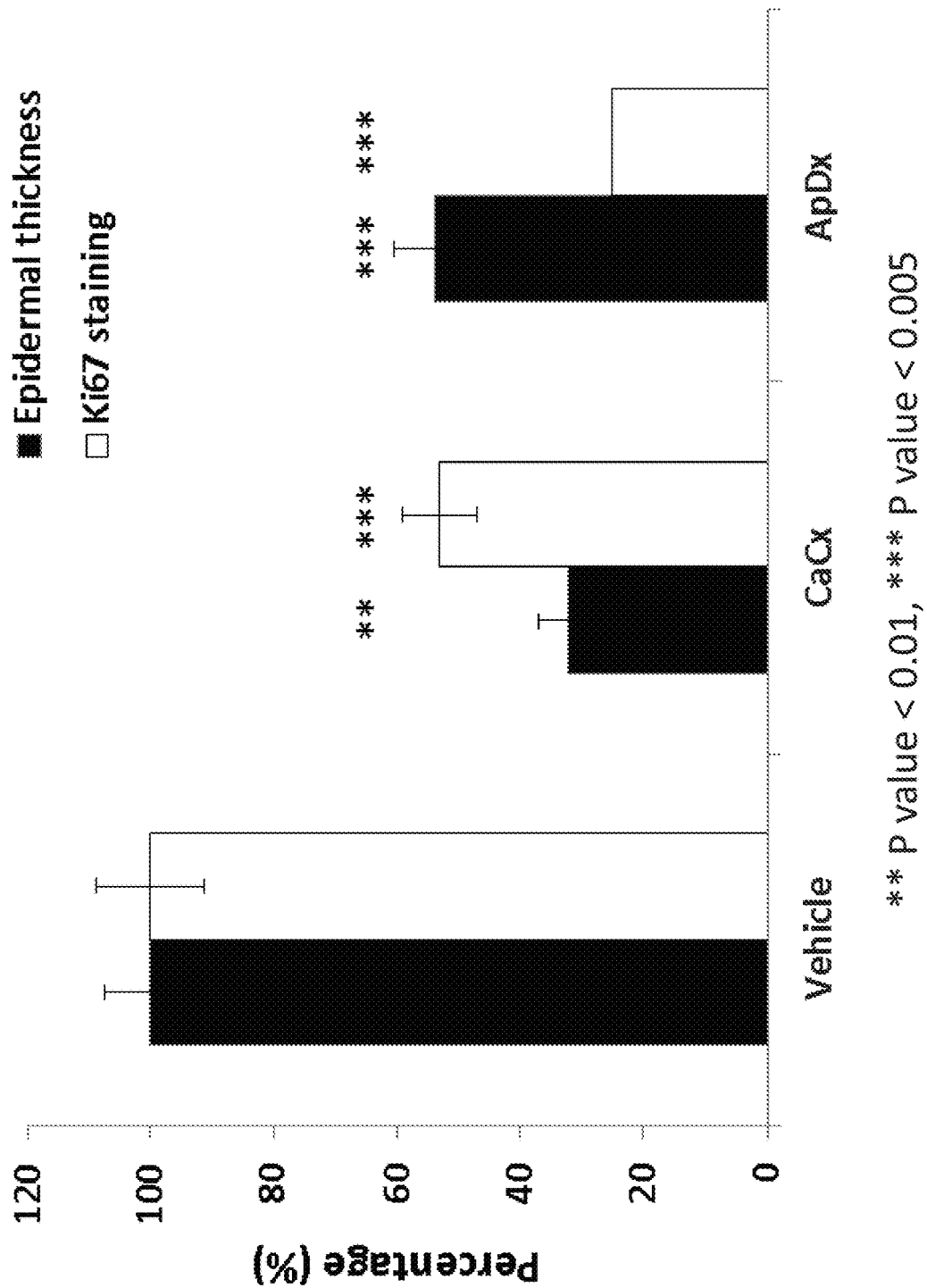

FIG. 8 illustrates Ki67 staining and epidermal thickness in chimeric mice carrying human psoriatic skin after treatment with CaCx and ApDx. Mice were treated as described in FIGS. 7A-F, above. Epidermal thickness measured in micrometers (black columns) and the percentage of positive Ki67 in the epidermis (white columns) is shown.

Figure 9:
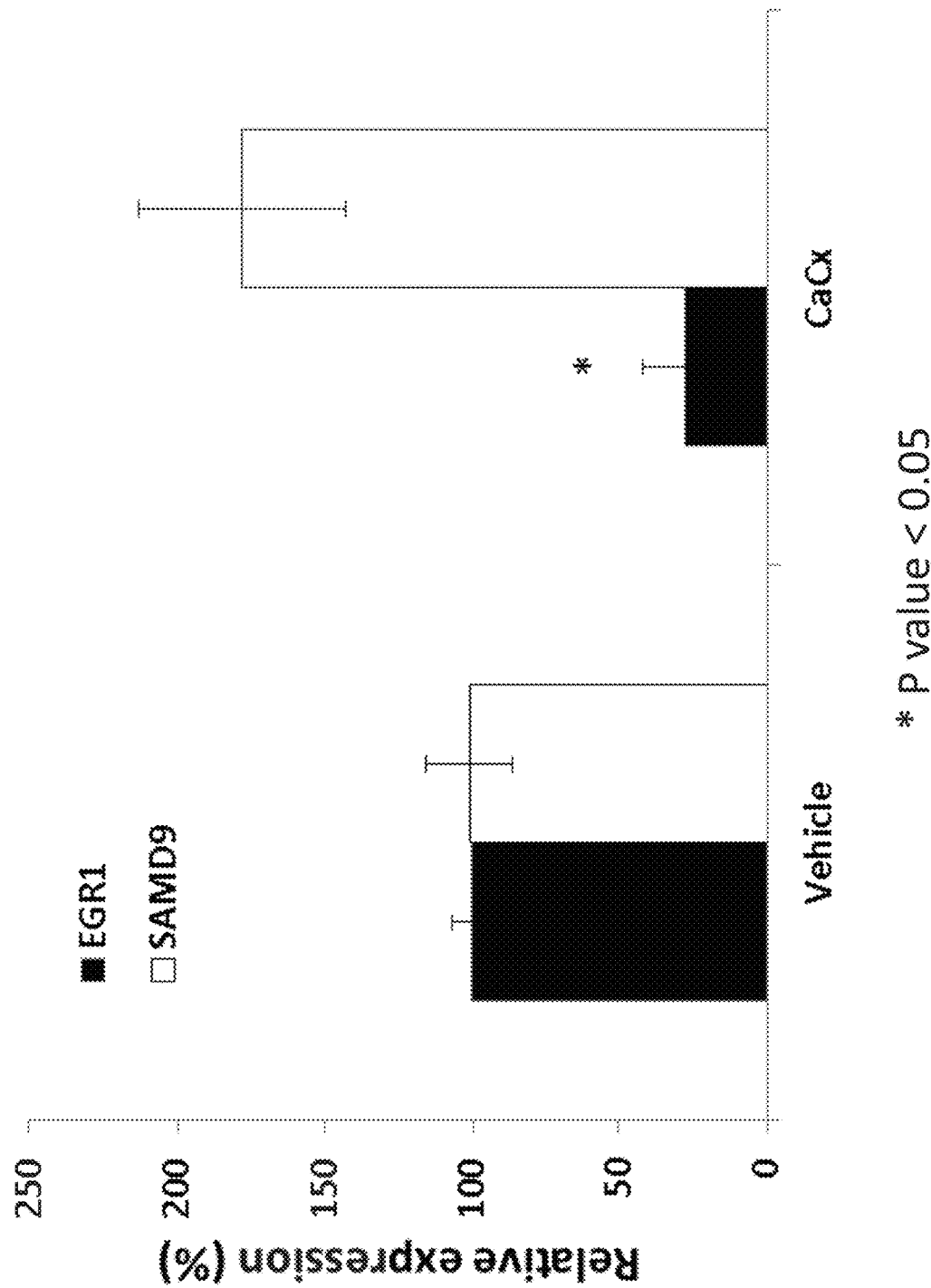

FIG. 9 illustrates EGR1 and SAMD9 RNA levels in chimeric mice carrying human psoriatic skin after treatment with CaCx. Mice were treated as described in FIGS. 7A-F, above. EGR1 (black columns) and SAMD9 (white columns) RNA levels were measured in triplicates by qRT-PCR. Results are expressed as RNA expression relative to control mice treated with the vehicle treated group±standard error. *=$p<0.05$; **=$p<0.01$.

DESCRIPTION OF SPECIFIC EMBODIMENTS OF THE INVENTION

The present invention, in some embodiments thereof, relates to therapy and, more particularly, but not exclusively, to EGR1 targeting drugs and to use thereof for the treatment of inflammatory and hyperproliferative conditions.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Conventional treatments for inflammation do not fundamentally cure inflammation, and are often endowed with side effects such as hypersensitivity reaction, and deterioration of immune system.

Psoriasis, a chronic inflammatory disease, affects about 2-3% of the world population. To date there is no cure for psoriasis.

Some of the present inventors have previously uncovered that loss of expression or function of SAMD9 leads to inflammation and subsequent calcinosis. SAMD9 functions by down-regulating the expression of EGR1, a critical regulator of inflammatory responses.

While reducing the present invention to practice, the present inventors have uncovered through laborious experimentation and screening a class of small molecule inducers of SAMD9 transcriptional activity, which down-regulate EGR1 and as such can be used for the treatment of inflammatory and hyperproliferative diseases including skin diseases, such as psoriasis.

As described herein and in the Examples section which follows, the present inventors generated cell lines stably expressing a luciferase gene under the regulation of a functional SAMD9 promoter and used these cells for screening of over 1400 small molecules. About 85 of the screened molecules were shown to induce SAMD9-dependent luciferase activity in the initial screen. These molecules were further tested for induction of SAMD9 expression, and 31 exemplary compounds which were found active in both assays are presented in Table 2 hereinbelow. Two of these exemplary compounds, 6H-Pyrido[4,3-b]carbazole-1-carboxamide, 5,11-dimethyl-, monohydrochloride (CaCx) and 10-n-Propyl-1,3-dichloro-7-amino-phenothiazine-5,5-dioxide (ApDx), were further tested, and reproducibly induced SAMD9 promoter activity as well as endogenous SAMD9 expression in HeLa, TERC-transformed fibroblasts and primary fibroblasts cells in a time- and dose-dependent manner (FIGS. 1C, 2A and 2B). These two inducers of SAMD9 down-regulated the expression of EGR1 (FIG. 3). The two compounds were subsequently assessed in an in vivo murine model and were found to reverse the epidermal histopathological phenotype of imiquimod-induced psoriasiform dermatitis (FIGS. 4A-F and 5A-B). Moreover, the two compounds were shown to attenuate psoriasiform phenotype, as measured by clinical score and by histological examination, in a chimeric mouse model carrying human psoriatic skin (FIGS. 6, 7A-F, 8 and 9).

These data lead to the understanding that compounds which exhibit structural features as delineated hereinafter are useful as EGR1 targeting drugs and in the treatment of inflammation and hyperproliferative diseases or disorders, as described in further detail in the following.

Thus, according to one aspect of the present invention there is provided a method of treating an inflammation or a hyperproliferative disease in a subject in need thereof, the method comprising administering to the subject a therapeutically effective amount of a compound represented by Formula I, II or III, as described herein in any of the respective embodiments, thereby treating the inflammation or the hyperproliferative disease in the subject. According to another aspect of the present invention there is provided a use of a compound represented by Formula I, II or III, as described herein in any of the respective embodiments for the manufacture of a medicament identified for treating an inflammation or a hyperproliferative disease in a subject in need thereof. According to another aspect of the present invention, there is provided a compound represented by Formula I, II or III, as described herein in any of the respective embodiments, for use in the treatment of inflammation or a hyperproliferative disease in a subject in need thereof.

As used herein, the term "treating" refers to alleviating, attenuating, palliating or eliminating the symptoms of an inflammation or of a hyperproliferative disease, slowing, reversing or arresting the progression of the inflammation or the hyperproliferative disease, or curing the inflammation or the hyperproliferative disease.

As used herein, the term "subject" or "subject in need thereof" refers to a mammal, preferably a human being, male or female, at any age which suffers from the pathology or is at risk to develop the pathology.

According to one embodiment, the pathology is an inflammation or a hyperproliferative disease.

Inflammation

The term "inflammation" as used herein refers to the general term for local accumulation of fluids, plasma proteins, and white blood cells initiated by physical injury, infection, or a local immune response. Inflammation may be associated with several signs e.g. redness, pain, heat, swelling and/or loss of function. Inflammation is an aspect of many diseases and disorders, including but not limited to diseases related to immune disorders, viral and bacterial infection, arthritis, autoimmune diseases, collagen diseases, allergy, asthma, pollinosis, and atopy (as described in further detail below).

Thus, inflammation can be triggered by injury, for example injury to skin, muscle, tendons, or nerves. Inflammation can be triggered as part of an immune response, e.g., pathologic autoimmune response. Inflammation can also be triggered by infection, where pathogen recognition and tissue damage can initiate an inflammatory response at the site of infection.

Inflammation according to the present teachings may be associated with chronic (long term) inflammatory diseases or disorders or acute (short term) inflammatory diseases or disorders.

According to a specific embodiment, the inflammation is associated with a disease selected from the group consisting of an infectious disease, an autoimmune disease, a hypersensitivity associated inflammation, a graft rejection and an injury.

According to a specific embodiment, the inflammation comprises a skin inflammation.

According to a specific embodiment the skin inflammation is psoriasis.

Diseases characterized by inflammation of the skin, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis, rosacea, psoriasis and acne. Inflammation can also result from physical injury to the skin.

Inflammation may be triggered by various kinds of injuries to muscles, tendons or nerves. Thus, for example, inflammation may be caused by repetitive movement of a part of the body i.e. repetitive strain injury (RSI). Diseases characterized by inflammation triggered by RSI include, but are not limited to, bursitis, carpal tunnel syndrome, Dupuytren's contracture, epicondylitis (e.g. tennis elbow), ganglion (i.e. inflammation in a cyst that has formed in a tendon sheath, usually occurring on the wrist), rotator cuff syndrome, tendinitis (e.g., inflammation of the Achilles tendon), tenosynovitis, and trigger finger (inflammation of the tendon sheaths of fingers or thumb accompanied by tendon swelling).

Many diseases related to infectious diseases include inflammatory responses, where the inflammatory responses are typically part of the innate immune system triggered by the invading pathogen. Inflammation can also be triggered by physical (mechanical) injury to cells and tissues resulting from the infection. Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases. According to one embodiment, examples of infections characterized by inflammation include, but are not limited to, encephalitis; meningitis; encephalomyelitis; viral gastroenteritis; viral hepatitis.

Furthermore, many immune disorders include acute or chronic inflammation. For example, arthritis is considered an immune disorder characterized by inflammation of joints, but arthritis is likewise considered an inflammatory disorder characterized by immune attack on joint tissues.

Inflammation according to the present teachings may be associated with a deficient immune response (e.g., HIV, AIDS) or with an overactive immune response (e.g., allergy, autoimmune disorders). Thus, inflammation according to the present teachings may be associated with any of the following:

Inflammatory Diseases Associated with Hypersensitivity:

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2): 1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann NY Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Internet (Paris). 2000 May; 151 (3):178); antiphospholipid syndrome (Flamholz R. et al., J Clin Apheresis 1999; 14 (4):171); heart failure, agonist-like 0-adrenoceptor antibodies in heart failure (Wallukat G. et at, Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. el al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. el al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases:

Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Internet (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. el al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. el al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Komberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, the autoimmune disease is Crohn's disease, psoriasis, scleroderma or rheumatoid arthritis.

Graft Rejection Diseases:

Examples of diseases associated with transplantation of a graft include, but are not limited to, graft rejection, chronic graft rejection, subacute graft rejection, hyperacute graft rejection, acute graft rejection and graft versus host disease.

Allergic Diseases:

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Hyperproliferative Diseases:

The term "hyperproliferative disease" as used herein refers to any condition which involves uncontrolled cell growth, i.e. an abnormally high rate of proliferation of cells by rapid cell division.

The present invention is not limited to a particular type of hyperproliferative disease or disorder and may include tumors, cancers, neoplastic tissue as well as pre-malignant and non-neoplastic or non-malignant hyperproliferative disorders.

In some embodiments, the hyperproliferative disorder is a cancer including, but not limited to, carcinoma, lymphoma, blastoma, sarcoma, and leukemia. The cancer may include solid tumors, metastasis as well as mixed tumors. Particular examples of cancerous diseases but are not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, bladder cancer, leukemia (e.g. Myeloid leukemia such as Chronic myelogenous leukemia; Acute myelogenous leukemia with maturation; Acute promyelocytic leukemia; Acute nonlymphocytic leukemia with increased basophils; Acute monocytic leukemia; Acute myelomonocytic leukemia with eosinophilia), lymphoma (e.g. Malignant lymphoma, such as Birkitt's Non-Hodgkin's; Lymphoctyic leukemia, such as Acute lymphoblastic leukemia; Chronic lymphocytic leukemia), renal cancer, uterine cancer and ovarian cancer.

As mentioned the teachings of the present invention also contemplate the treatment of hyperproliferative diseases (e.g., cancer and psoriasis), which often associate with inflammation. According to one embodiment, the teachings of the present invention contemplate treatment of cancer e.g., metastatic cancer, also referred to as cancer metastasis.

According to one embodiment, the hyperproliferative disease is a calcified cancer or tumor. The calcified cancer or tumor according to one embodiment of the invention may be a normophosphatemic variant of familial tumoral calcinosis (NFTC).

Effect on SAMD9 and EGR1 Activity:

According to some embodiments of the invention, and without being bound by theory, it is suggested that the compounds as described herein are effective in activating SAMD9 to thereby downregulate EGR1 activity.

As used herein, the term SAMD9 refers to the sterile alpha motif domain containing 9, e.g., human SAMD9, e.g., as set forth in GenBank accession nos. NM_017654.3 or NM_001193307.1 and NP_060124.2 or NP_001180236.1 (mRNA and protein, respectively).

Thus, according to one embodiment, the compounds of the present embodiments upregulate the activity or expression of SAMD9 by about 10%, 20%, 30%, 40%, 50%, 60%, 70%, 80%, 90%, 100% or more, as compared to the activity or expression of the SAMD9 in a cell of the subject prior to the treatment (or in a corresponding sample of another subject having the same pathology and preferably matched with the same species e.g. human, age, weight, sex etc. as the subject in need thereof).

As used herein, the term EGR1 refers to the Early Growth Response protein 1 such as the human EGR1 e.g., as set forth in GenBank accession nos. NM_001964.2 and NP_001955.1 (mRNA and protein, respectively).

Thus, according to one embodiment, the compounds of the present invention downregulates an activity or expression of EGR1 by about 10%, 20%, 30%, 40%, 50%, 60%, 70%, 80%, 90% or 100% as compared to the activity or expression of the EGR1 in a cell of the subject prior to the treatment (or in a corresponding sample of another subject having the same pathology and preferably matched with the same species e.g. human, age, weight, sex etc. as the subject in need thereof).

The Compounds:

The compounds of the present embodiments are referred to interchangeably herein throughout as "compounds", "molecules", "therapeutically active agents", "drugs" or "EGR1 targeting drugs".

Compounds useful within any one of the embodiments described herein, can be collectively represented by Formula I, II or III, as described herein.

According to some of any of the embodiments described herein, compounds useful in any of the methods and uses described herein are collectively represented by Formula I:

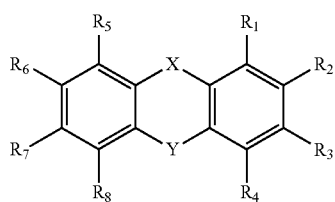

Formula I or a pharmaceutically acceptable salt thereof, as defined herein,
wherein:
X is N—$R_9$;
Y is selected from S(=O)$_2$, C=O, or is absent;
$R_1$-$R_8$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively or in addition, two of $R_1$-$R_4$ and $R_9$ and/or $R_5$-$R_9$ form together a cyclic ring, said cyclic ring being selected from aryl, heteroaryl, cycloalkyl or heteroalicyclic.

According to some embodiments, Y is S(=O)$_2$.
According to some of these embodiments, $R_9$ is hydrogen (H).
According to some of these embodiments, $R_9$ is alkyl, such as, methyl, ethyl, propyl, isopropyl, butyl, etc.
According to some embodiments, Y is S(=O)$_2$, and $R_9$ is alkyl, for example, propyl.
According to some embodiments, $R_1$-$R_4$ are each hydrogen.
According to some embodiments, at least one of $R_1$-$R_4$ is a substituent (i.e., other than hydrogen).
According to some embodiments, at least one of $R_1$-$R_4$ is halo, for example, chloro.
According to some embodiments, at least two of $R_1$-$R_4$ are independently a halo, for example, chloro.
According to some embodiments, Y is S(=O)$_2$, and $R_9$ is alkyl, for example, propyl, $R_1$ and $R_4$ are each hydrogen and $R_3$ and $R_2$ are each chloro.
According to some of these embodiments, each of $R_5$-$R_8$ is hydrogen. Such a compound is referred to herein as ApDx.
Alternatively, one or more of $R_5$-$R_8$ is a substituent (i.e., other than hydrogen).
Further alternatively, for any of the embodiments described herein for compounds of Formula I, two of $R_1$-$R_4$ and $R_9$ and/or $R_5$-$R_9$ form together a cyclic ring. Herein, a "cyclic ring" describes typically a 5- or -membered ring, optionally substituted. The formed ring, by its definition, is fused to one or more of the aromatic rings and/or to the middle ring therebetween.

Depending on the substituents forming the ring, the ring can be carbocyclic, namely, an aromatic ring (a substituted or unsubstituted aryl, as defined herein) or a non-aromatic ring (a substituted or unsubstituted cycloalkyl, as defined herein), optionally fused to another ring, as described herein, or a heterocyclic ring, namely, a substituted or unsubstituted heteroalicyclic, as defined herein or a heteroaromatic ring (a substituted or unsubstituted hereteroaryl, as defined herein), optionally fused to another ring, as described herein.

For example, when $R_9$ and $R_1$ form a ring, the ring is heterocylic.
When two of $R_1$-$R_4$ form a ring, and one or more of $R_1$-$R_4$ is amine, hydroxyl, thiol, sulfate, sulfonate, amide, etc., the formed ring is heterocylic.
When two of $R_1$-$R_4$ form a ring, and each is alkyl, the formed ring is carbocylic.
According to some embodiments related to Formula I herein, Y is C(=O).
According to some of these embodiments, $R_9$ is hydrogen (H).
According to some of these embodiments, $R_9$ is alkyl, such as, methyl, ethyl, propyl, isopropyl, butyl, etc.
According to some of these embodiments, $R_1$-$R_4$ are each hydrogen.
According to some of these embodiments, at least one of $R_1$-$R_4$ is a substituent (i.e., other than hydrogen).
According to some embodiments, at least one of $R_1$-$R_4$ is an amine, preferably a substituted amine.
According to some embodiments, Y is C(=O), and $R_9$ is alkyl, $R_1$ and $R_4$ are each a substituted amine and $R_3$ and $R_2$ are each hydrogen.
According to some of these embodiments, each of $R_5$-$R_8$ is hydrogen.
Alternatively, one or more of $R_5$-$R_8$ is a substituent (i.e., other than hydrogen).
According to some of these embodiments, one or more of $R_5$-$R_9$ is a substituent such as hydroxyl, thiol, alkoxy or thioalkoxy, as defined herein.
Further alternatively, for any of the embodiments described herein for compounds of Formula I, two of $R_1$-$R_4$ and $R_9$ and/or $R_5$-$R_9$ form together a cyclic ring.
According to some embodiments, $R_1$ and $R_9$ form together a cyclic ring.
According to some of these embodiments, $R_1$ and $R_9$ form together a heterocylic ring, and in some embodiments, the heterocylic ring is a heteroaryl.
In some of any of the embodiments of Formula I described herein, Y is C(=O), $R_1$ and $R_9$ form together a heteroaryl, and the heteroaryl is a 1H-imidazole, optionally 2-methyl-1H-imidazole, being fused to both the aromatic ring bearing $R_1$ and the ring bearing $R_9$, thus forming a completely conjugated tricyclic aromatic system, as depicted for compound 637993 in Table 2.
In some of these embodiments, $R_7$ is methoxy, although any other substituents as described herein is contemplated.
In some of these embodiments, $R_3$ is a substituted amine, and the amine is preferably substituted by an amino alkyl. In some embodiments, the aminoalkyl is a dialkylaminoalkyl, as depicted, as a non-limiting example, for compound 637993 in Table 2.
According to some embodiments, such compounds are useful in the treatment of inflammation or hyperproliferative diseases as described herein, which are other than cancer.

According to some of the embodiments related to Formula I as described herein, Y is absent. Such compounds have a five-membered ring fused to and posed between the aromatic rings in Formula I.

According to some of these embodiments, $R_9$ is H.

According to some of these embodiments, $R_9$ is alkyl, such as, methyl, ethyl, propyl, isopropyl, butyl, etc., and in some embodiments, $R_9$ is a substituted alkyl.

In some embodiments, $R_9$ is a substituted alkyl, and the substituent is O-carboxylate, as described herein. In some embodiments the alkyl is substituted by benzoate. In some embodiments, $R_9$ is ethyl benzoate.

In some of any of the embodiments of Formula I as described herein, when Y is absent, each of $R_1$-$R_4$ is hydrogen. However, one or more of $R_1$-$R_4$ can be a substituent as described herein, or two or more can form a ring, as described herein.

In some of any of the embodiments of Formula I as described herein, when Y is absent, one or more of $R_5$-$R_8$ is alkyl. In some embodiments $R_5$ and $R_8$ are each independently an alkyl and in some embodiments, each of $R_5$ and $R_8$ is methyl.

In some of any of the embodiments of Formula I as described herein, when Y is absent, two or more of $R_5$ and $R_8$ form a cyclic ring, as defined herein, and in some embodiments, the cyclic ring is a heteroaryl, for example, pyridine. In some of these embodiments, $R_6$ and $R_7$ form pyridine.

In some embodiments of Formula I, Y is absent, $R_9$ is as described herein, $R_1$-$R_4$ are each hydrogen, $R_5$ and $R_8$ are each alkyl such as methyl, and $R_6$ and $R_7$ form a ring, preferably, pyridine. An exemplary such compound in ApDx (see, Table 2). Another exemplary compound is compound 163433 in Table 2.

In some embodiments, such compounds are useful in the treatment of inflammation and hyperproliferative diseases as described herein, whereby the disease is other than a parasitic disease (a disease caused by a parasite).

According to some of any of the embodiments described herein, compounds useful in any of the methods and uses described herein are collectively represented by Formula II:

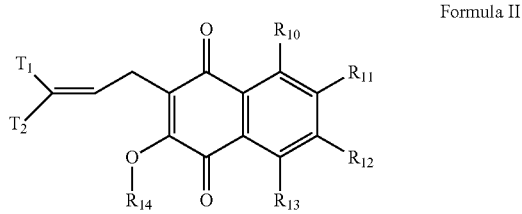

Formula II wherein:
$R_{10}$-$R_{13}$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively, two of $R_{10}$-$R_{13}$ form together a cyclic ring, said cyclic ring being selected from aryl, heteroaryl, cycloalkyl or heteroalicyclic;
$R_{14}$ is hydrogen, alkyl or cycloalkyl; and
$T_1$ and $T_2$ are each halo.

In some of these embodiments, $R_{10}$-$R_{13}$.
In some embodiments, $R_{14}$ is hydrogen.
In some embodiments, $T_1$ and $T_2$ are each chloro.
In some of these embodiments, the compound is Dichlorolawsone (see compound 126771 in Table 2), a natural extracted compound.

According to some of any of the embodiments described herein, compounds useful in any of the methods and uses described herein are collectively represented by Formula

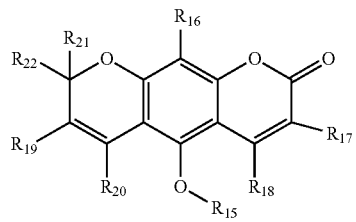

Formula III wherein:
$R_{15}$ is hydrogen, alkyl or cycloalkyl;
$R_{16}$-$R_{22}$ are each independently hydrogen, alkyl, cycloalkyl, halo, trihaloalkyl, amino, alkoxy, thioalkoxy, hydroxyl, thiol, nitro, cyano, aryl, or heteroaryl, or, alternatively, two of $R_{15}$, $R_{17}$ and $R_{18}$ and/or two of $R_{15}$, $R_{19}$-$R_{22}$ form together a cyclic ring, said cyclic ring being selected from aryl, heteroaryl, cycloalkyl and heteroalicyclic.

In some of these embodiments, $R_{15}$ is methyl.
In some of any of these embodiments, $R_{17}$ and $R_{18}$ are each hydrogen.
In some of any of these embodiments, $R_{17}$ and $R_{18}$ are each hydrogen.
In some of any of these embodiments, one or both $R_{21}$ and $R_{22}$ is alkyl. In some embodiments, each of $R_{21}$ and $R_{22}$ is alkyl, and in some embodiments the alkyl is methyl.

Such a compound is known as Xanthoxylin N (see, compound 35542 in Table 2).

According to some embodiments, when the compound is represented by Formula II or III, the inflammation or hyperproliferative disease is not associated with microbial infection.

For any of the embodiments described herein, the compound may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of the compound is modified by an acyl group, optionally ($C_{1-4}$)acyl (e.g., acetyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any isomorph of a compound as described herein, when the compound exhibits polymorphism.

Pharmaceutical Compositions:

The compounds (EGR1 targeting drugs) of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the EGR1 targeting drug accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to one embodiment, the EGR1 targeting drugs are formulated for cutaneous e.g., topical administration (e.g., to a keratinous tissue, such as the skin, scalp), subcutaneous, dermal transdermal administration. For example, the pharmaceutical composition of some embodiments of the invention is formulated as a cream, lotion, spray, ointment, salve, gel, oil, wash, etc. for applying or spreading onto the surface of the body, i.e. skin, scalp, hair, nails and the like, preferably on the surface or in close proximity to the inflammation (e.g. psoriasis).

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

For topical administration, the pharmaceutical composition can be formulated in any of a variety of forms utilized by the pharmaceutical industry for skin application including solutions, lotions, sprays, creams, ointments, salves, gels, oils, wash, etc., as described below.

The pharmaceutical compositions of the present invention may be formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including but not limited to lotions and creams, may comprise a dermatologically acceptable emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. Exemplary emollients include, but are not limited to, glycerin, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like.

The topically applied pharmaceutical composition of the present invention may also include additional components which are added, for example, in order to enrich the pharmaceutical compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The pharmaceutical compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

The pharmaceutical composition may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an adhesive bandage, a non-adhesive bandage, a wipe, a baby wipe, a gauze, a pad and a sanitary pad.

The quantity of active compound in a unit dose of preparation may be varied or adjusted according to the particular application.

Pharmaceutical compositions suitable for use in context of some embodiments of the invention include compositions wherein the active ingredients are contained in an amount effective to achieve the intended purpose. More specifically, a therapeutically effective amount means an amount of active ingredients (EGR1 targeting drug) effective for preventing, treating or reducing the inflammatory response (e.g. anti-inflammatory effect) or hyperproliferative disease (e.g. anti-tumor effect) or prolonging the survival of the subject being treated. A "therapeutically effective amount" of an EGR1 targeting drug may be determined in a routine manner by any method known to one of skill in the art (e.g. blood test, ultrasound, X-ray, CT scan, MRI, etc.).

Thus, determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide ample levels of the active ingredient sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the article of manufacture may further comprise another active ingredient to improve therapeutic efficacy. Thus for example the molecules of the present invention may be administered in combination with an anti-cancer therapeutic, e.g. a chemotherapeutic agent, immunotherapy, radiotherapy, and/or with an agent for the treatment of inflammation, e.g. anti-inflammatory agent. Thus, for example, the EGR1 targeting drug can be packaged in one container while the chemotherapeutic agent or anti-inflammatory agent may be packaged in a second container both for therapeutic treatment.

According to one embodiment, the EGR1 targeting drug and the chemotherapy are in a co-formulation.

According to another embodiment, the EGR1 targeting drug and the anti-inflammatory agent are in a co-formulation.

As used herein, the terms "chemotherapy" or "chemotherapeutic" refer to an agent that reduces, prevents, mitigates, limits, and/or delays the growth of neoplasms or metastases, or kills neoplastic cells directly by necrosis or apoptosis of neoplasms or any other mechanism, or that can be otherwise used, in a pharmaceutically-effective amount, to reduce, prevent, mitigate, limit, and/or delay the growth of neoplasms or metastases in a subject with neoplastic disease (e.g. cancer).

Chemotherapeutic agents include, but are not limited to, fluoropyrimidines; pyrimidine nucleosides; purine nucleosides; anti-folates, platinum agents; anthracyclines/anthracenediones; epipodophyllotoxins; camptothecins (e.g., Karenitecin); hormones; hormonal complexes; antihormonals; enzymes, proteins, peptides and polyclonal and/or monoclonal antibodies; immunological agents; *vinca* alkaloids; taxanes; epothilones; antimicrotubule agents; alkylating agents; antimetabolites; topoisomerase inhibitors; antivirals; and various other cytotoxic and cytostatic agents.

According to a specific embodiment, the chemotherapeutic agents include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer, Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper, Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur, Talisomycin; Taxol; Tecogalan Sodium; Tegafur, Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

In order to enhance treatment of the cancer, the present invention further envisions administering to the subject an additional therapy such as radiotherapy, chemotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. Analgesic agents and other treatment regimens are also contemplated.

As used herein, the terms "anti-inflammatory" refer to an agent that prevents or reduces the inflammatory response, or which soothes inflammation by reducing the symptoms of inflammation such as redness, pain, heat, or swelling.

Anti inflammatory drugs that can be administered in combination with the EGR1 targeting drug of some embodiments of the invention include, but are not limited to Alclofenac; Alclometasone Dipropionate; Algestone Acetonide; Alpha Amylase; Amcinafal; Amcinafilde; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Compositions (EGR1 targeting drug and/or optionally anti cancer or anti-inflammatory agent, such as described above) of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Definitions

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

When an amine forms a part of a ring, as, for example, in Formula I, its substituents are as defined herein for Formula I.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene and Alkyne, as used herein, are an alkyl, as defined herein, which contains one or more double bond or triple bond, respectively.

Whenever an alkyl group is described herein as a substituent, it can be replaced by alkene or alkyne, as described herein.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, 0-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "halide" and "halo" describes fluorine, chlorine, bromine or iodine.

The term "haloalkyl" describes an alkyl group as defined above, further substituted by one or more halide. A trihalo alkyl, such as trihalomethyl describes a —$CT_3$ group, wherein each T is halo.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "nitro" describes an —$NO_2$ group.

The term "sulfate" describes a —O—S(═O)$_2$—OR' end group, as this term is defined hereinabove, or an —O—S(═O)$_2$—O— linking group, as these phrases are defined hereinabove, where R' is as defined hereinabove.

The term "thiosulfate" describes a —O—S(═S)(═O)—OR' end group or a —O—S(═S)(═O)—O— linking group, as these phrases are defined hereinabove, where R' is as defined hereinabove.

The term "sulfite" describes an —O—S(═O)—O—R' end group or a —O—S(═O)—O— group linking group, as these phrases are defined hereinabove, where R' is as defined hereinabove.

The term "thiosulfite" describes a —O—S(═S)—O—R' end group or an —O—S(═S)—O— group linking group, as these phrases are defined hereinabove, where R' is as defined hereinabove.

The term "sulfinate" describes a —S(═O)—OR' end group or an —S(═O)—O— group linking group, as these phrases are defined hereinabove, where R' is as defined hereinabove.

The term "sulfoxide" or "sulfinyl" describes a —S(═O)R' end group or an —S(═O)— linking group, as these phrases are defined hereinabove, where R' is as defined hereinabove.

The term "sulfonate" describes a —S(═O)$_2$—R' end group or an —S(═O)$_2$— linking group, as these phrases are defined hereinabove, where R' is as defined herein.

The term "S-sulfonamide" describes a —S(═O)$_2$—NR'R" end group or a —S(═O)$_2$—NR'— linking group, as these phrases are defined hereinabove, with R' and R" as defined herein.

The term "N-sulfonamide" describes an R'S(═O)$_2$—NR"— end group or a —S(═O)$_2$—NR'— linking group, as these phrases are defined hereinabove, where R' and R" are as defined herein.

The term "carbonyl" or "carbonate" as used herein, describes a —C(═O)—R' end group or a —C(═O)— linking group, as these phrases are defined hereinabove, with R' as defined herein.

The term "thiocarbonyl" as used herein, describes a —C(═S)—R' end group or a —C(═S)— linking group, as these phrases are defined hereinabove, with R' as defined herein.

The term "oxo" as used herein, describes a (═O) group, wherein an oxygen atom is linked by a double bond to the atom (e.g., carbon atom) at the indicated position.

The term "thiooxo" as used herein, describes a (═S) group, wherein a sulfur atom is linked by a double bond to the atom (e.g., carbon atom) at the indicated position.

The term "oxime" describes a ═N—OH end group or a ═N—O— linking group, as these phrases are defined hereinabove.

The term "acyl halide" describes a —(C═O)R"" group wherein R" is halide, as defined hereinabove.

The term "azo" or "diazo" describes an —N═NR' end group or an —N═N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(═O)—OR' end group or a —C(═O)—O— linking group, as these phrases are defined hereinabove, where R' is as defined herein.

The term "O-carboxylate" describes a —OC(═O)R' end group or a —OC(═O)-linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(═S)—OR' end group or a —C(═S)—O— linking group, as these phrases are defined hereinabove, where R' is as defined herein.

The term "O-thiocarboxylate" describes a —OC(═S)R' end group or a —OC(═S)-linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and 0-carbamate.

The term "N-carbamate" describes an R"OC(═O)—NR'— end group or a —OC(═O)—NR'— linking group, as these phrases are defined hereinabove, with R' and R" as defined herein.

The term "O-carbamate" describes an —OC(═O)—NR'R" end group or an —OC(═O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and 0-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)-linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for Materials and Experimental Procedures Cell Cultures:

HeLa cells were cultured in DMEM 4.5 g/l glucose medium containing 10% FCS, 1% L-glutamine and 1% penicillin and streptomycin (Biological Industries) and grown at 37° C. and 5% $CO_2$.

TERC-transformed fibroblasts were transformed with a pBABE-H2AGFP construct containing the human telomerase gene were cultured High Glucose DMEM, 10% FCS, L-glutamine and Pen-Strep (all cell culture regents from Biological Industries, Israel). Medium was changed every 2-3 days. Cells were used at passage 2-3.

Primary fibroblasts were isolated from human adult skin and were grown in High Glucose DMEM, 10% Fetal Bovine Serum, L-glutamine and Pen-Strep. Medium was changed every 2-3 days. Cells were used at passage 2-3.

Of note, when cells were incubated with CaCx and ApDx (NCI, MA USA), they were grown in the appropriate medium with 0.1% FCS only.

Animals:

Balb/c mice (Harlan Laboratories Ltd, Jerusalem, Israel), 9 weeks of age, were maintained in a pathogen-free animal facility. Animal care and research protocols had been approved by the institutional committee for animal use. Imiquimod 5% (Perrigo, Israel) was used as topical treatment for the mice on their upper backs. Mice were injected i.p. five times a week with DMSO or 7.5-22.5 mg/kg of ApDx and CaCx, respectively (NCI). 10% DMSO in lipofuscin was used as a vehicle control.

Chimeric Mice:

Chimeric mice carrying human psoriatic skin were generated using SCID mice, 2-3 months of age. Animals were maintained in a pathogen-free animal facility. A psoriasis-like phenotype was induced in normal human skin grafted onto the mice by intradermal injection of natural killer/T cells derived from psoriatic patients as previously described [Gilhar A et al. J Invest Dermatol (2011) 131: 118-124].

Light Microscopy and Immunohistochemistry:

Formaldehyde-fixed 5-μm paraffin-embedded sections from skin biopsies were deparaffinized and treated with 3% $H_2O_2$ in methanol for 15 minutes at room temperature, warmed in a microwave oven in citrate buffer in a pressure cooker for 25 minutes, and stained with a monoclonal anti-Ki67 antibody (Thermo Scientific) for 1 hour at room temperature. Following 3 washings (10 minutes each) with phosphate-buffered saline (PBS), the antibodies were imaged using the ABC technique (Zymed Laboratories, South San Francisco, CA) and the slides were counterstained with hematoxylin.

Epidermal thickness was defined as the distance between the granular layer and the basement membrane and was measured at 10 randomly selected locations for each biopsy using NIS-Elements BR 3.2 software (Nikon, NY USA). An image was taken and was manually measured in the software by selecting an upper and lower border, as defined above. The distance was measured in microns.

Quantitative Reverse Transcription PCR (qRT-PCR):

RNA was extracted from cell cultures using an RNA extraction kit (Roche Diagnostics, Mahheim, Germany). cDNA was synthesized from 500 ng of total RNA using the Verso cDNA kit (Thermo Fisher Scientific, Waltham, MA, USA). cDNA PCR amplification was carried out using the Fast SYBR Green Master Mix in a StepOnePlus™ Real-Time PCR System (Applied Biosystems, Foster City, CA, USA) with gene-specific intron-crossing oligonucleotide pairs listed in Table 1 (below). For quantification, standard curves were obtained using serially diluted cDNA amplified in the same qRT-PCR run. The melting temperature (Tm) of the amplified products was measured to confirm the specificity of the reaction conditions. Cycling conditions were as follows: 95° C. for 10 minutes, 95° C. for 10 seconds, 62° C. for 15 seconds, and 72° C. for 25 seconds for a total of 40 cycles. Each sample was analyzed in triplicate. mRNA expression level for target gene was normalized to GAPDH. The results are based the amount of target, normalized to an endogenous reference (IACTB) and relative to a calibrator, as calculated by 2-ΔΔCT. All samples were run in triplicate. The expression levels of target genes were expressed as mRNA relative units.

TABLE 1

Oligonucleotide sequences.

| Gene Name | Sequence | SEQ ID NO. |
|---|---|---|
| SAMD9 F | 5'-CGAGCAAGGTCCTTCCATAGTG-3' | 1 |
| SAMD9 R | 5'-CCGATGACCTCACAGCTCAAG-3' | 2 |
| EGR1 F | 5'-GGGCAGTCGAGTGGTTTGG-3' | 3 |
| EGR1 R | 5'-TTGCCGACAGGATGCAGAAGGA-3' | 4 |

Plasmids and Expression Constructs:

SAMD9 promoter fragments cloned into pGL3 as previously described [Hershkovitz, D. et al. (2011) J Invest Dermatol 131: 662-9], were digested with KpnI and XhoI and subcloned into pGL4.17 [luc2/Neo] (Promega). The expression vector pGL4.17 encodes the luciferase reporter gene luc2 (Photinuspyralis) and contains a mammalian selectable marker for neomycin resistance. For transient transfection, SAMD9 promoter-luciferase constructs were transfected into HeLa cells using lipofectamine 2000 (Invitrogen, Carlsbad, CA) according to the manufacturer's instructions.

HeLa cell lines stably expressing the constructs were generated under neomycin selection. Briefly, pGL4.17 containing a SAMD9 promoter fragment spanning 585 bp upstream to the TSS and an empty pGL4.17 vector were transfected into HeLa cells. Forty eight hours after transfection, standard medium was replaced with medium containing 600 μg/ml G418 (Sigma-Aldrich), cells were kept under G418 selection and the selective medium was replaced approximately every 2-3 days. After two passages, colonies of stable cells were isolated, expanded and frozen for further use.

Dual Luciferase Reporter Assay:

Cellular protein was extracted by adding 20 μl of Promega Lysis Buffer (PLB) (Promega) to each sample and incubated for a period of 15 minutes. Cell lysate was analyzed in a 96-well flat white plate (Greiner Bio-One, United Kingdom) where 100 μl of Luciferase Assay Reagent II (LAR II) (Promega) was added to each sample. Luminescence was ascertained using the Infinite M200 multimode microplate reader (Tecan Ltd, Minnedorf, Switzerland). After the initial reading, 100 μl of Stop & GloR Reagent (Promega) were dispensed into tested wells and Renilla luciferase levels were tested. The assay was completed after Luciferase levels were normalized to Renilla levels.

High-Throughput Screening for Identification of an SAMD9 Up-Regulator:

Test drugs were dispensed at a concentration of 10 μM by a robotic system into 96-well plates containing 9000 cells/well expressing the pGL4.17 reporter construct carrying a 585 bp SAMD9 promoter fragment operably linked to luciferase gene or the empty pGL4.17 luciferase construct (Promega cat. no. E6721). Medium was removed after 24 hours and the cells subjected to Steady-Glo luciferase lysis-substrate solution assay (Promega) as described above. Liquid handling was done with the Tecan (Tecan) Freedom 150 (Robotic & MCA liquid Handling System) and the luciferase reading was done with a robot integrated Tecan Infinite® M1000 reader.

Example 1

High-Throughput Screening for Inducers of SAMD9 Expression

SAMD9 promoter activity was first analyzed using a luciferase reporter assay in HeLa cells. A fragment (SEQ ID NO: 5) spanning 585 bp upstream to the SAMD9 predicted transcription start site (TSS) was cloned into pGL4 and co-transfected with pRL-TK *renilla* luciferase (hRluc) into HeLa cells. Forty eight (48) hours after transfection, the promoter activity was ascertained by measuring luciferase activity. The construct was assayed in the presence and absence of IFN-γ (10 ng/ml), which was previously identified as a strong inducer of SAMD9 expression [Hershkovitz, D. et al. (2011), supra]. IFN-γ significantly induced SAMD9 promoter activity (FIG. 1A). A stable HeLa cell line constitutively expressing the firefly luciferase gene under the regulation of the −585 bp SAMD9 promoter fragment was then generated, which was found to respond robustly to IFN-γ (FIG. 1B).

This cell line was then used to robotically screen a total of 1496 compounds obtained from the National Cancer Institute Diversity Set III and Oncology Drugs Set III small molecule libraries. Out of 85 compounds which were found to induce luciferase activity in the initial screen, 31 were observed to reproducibly induce SAMD9 promoter activity in the reporter HeLa cell line by more than two-fold (see, Table 2, hereinbelow).

Example 2

Effect of CaCx and ApDx on SAMD9 Expression in Human Cell Cultures

The potential ability of these 31 molecules to induce SAMD9 expression in cell cultures was then scrutinized. The data is presented in Table 2 hereinbelow. Two compounds, 6H-Pyrido[4,3-b]carbazole-1-carboxamide, 5,11-dimethyl-, monohydrochloride (CaCx) and 10-n-Propyl-1,3-dichloro-7-amino-phenothiazine-5,5-dioxide (ApDx) were found to significantly induce SAMD9 expression in HeLa cells, TERC-transformed fibroblasts and primary fibroblasts (FIG. 1C). CaCx and ApDx-mediated SAMD9 up-regulation was found to be both dose and time dependent (FIGS. 2A-B). Of note, each compound displayed a different optimal dose and time curve.

Both compounds significantly down-regulated EGR1 expression in primary fibroblast cells, albeit at different time points (FIG. 3).

Example 3

Effect of Systemic Administration of CaCx and ApDx on Imiquimod-Induced Psoriasiform Dermatitis in Mice The ability of CaCx and ApDx to down-regulate the expression of EGR1, a major mediator of inflammatory responses in the skin, suggested that these compounds may serve as anti-inflammatory drugs. This hypothesis was tested in a murine model in which psoriasiform dermatitis was induced using imiquimod [as previously described in Tortola, L. et al. (2012) J Clin Invest 122, 3965-76].

Balb/c mice were treated topically with imiquimod and were injected five times a week i.p. with either the vehicle, 22.5 mg/kg of CaCx or 7.5 mg/kg of ApDx.

After 5 days, biopsies were obtained from the treated skin and stained for hematoxylin and eosin as well as for Ki67 (FIGS. 4A-F), as a surrogate marker for cellular proliferation. Treatment with either compound resulted in a decrease in epidermal thickness, in the index of proliferation (FIG. 5A) but did not affect the inflammatory infiltrate. No overt toxicity was observed with either compound.

Quantitative PCR demonstrated a significant decrease in EGR1 (FIG. 5B) and IL-33 (an important inflammatory marker in the skin, FIG. 5C) RNA levels in both CaCx- and ApDx-treated skin.

Example 4

Chimeric Mice In-Vivo Experiment

To assess the potential therapeutic role of the compounds (ApDx and CaCx) of some embodiments of the invention, the two compounds were administered systemically (i.p) to chimeric mice carrying human psoriatic skin. In short, SCID mice, 2-3 months of age, were maintained in a pathogen-free animal facility. A psoriasis-like phenotype was induced in normal human skin grafted onto the mice by intradermal injection of natural killer/T cells derived from psoriatic patients as previously described [Gilhar A et al. J Invest Dermatol (2011) 131: 118-124]. Two weeks after natural killer/T-cell injection (6 weeks after human skin grafting), mice were injected i.p. five times a week. Four groups of mice were treated as follows: one group of mice was injected five times a week with the vehicle; a second group of mice was injected five times a week ApDx (5 mg/kg); a third group of mice was injected five times a week CaCx (15 mg/kg); and a fourth group of mice, was treated with dexamethasone (DEX) cream applied 5 times a week on the graft, as positive control (DEX was expected to attenuate inflammation in this model). Each group included five mice, and the treatment was performed for a total of 10 days. The grafts were harvested from the four groups of mice, paraffin-embedded, stained for hematoxylin and eosin (H&E), analyzed and scored for the average improvement of the clinical and histological psoriasiform phenotype.

As illustrated in FIG. 6, the results showed that both compounds (ApDx and CaCx) resulted in significant clinical and histological attenuation of the psoriasiform phenotype (ApDx p<0.0001, CaCx p<0.05). Furthermore, biopsies obtained from CaCx- or ApDx-treated skin after 10 days and stained for hematoxylin and eosin as well as for Ki67, as a surrogate marker for cellular proliferation, illustrated a significant decrease in epidermal thickness and in keratinocyte proliferation in chimeric mice carrying human psoriatic skin (FIGS. 7A-F and FIG. 8). No overt toxicity was observed with either compound. Moreover, quantitative PCR demonstrated a significant decrease in EGR1 RNA levels in CaCx-treated skin (FIG. 9).

Taken together, these results suggest that EGR1-targeting therapies may serve as an alternative or as an adjunct to current therapies for hyperproliferative skin inflammatory diseases.

TABLE 2

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 629971 | 7,9-dichloro-5,5-dioxo-10-propylphenothiazin-3-amine (ApDx) | 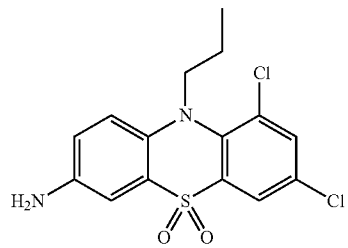 [SMILES: CCCN1c2ccc(N)cc2S(=O)(=O)c2cc(Cl)cc(Cl)c21] | 4.85 | 20.5 |
| 268242 | N,N-Dibenzyldaunorubicin hydrochloride | 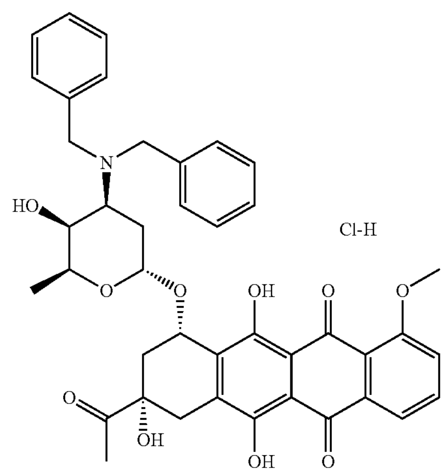 | 4.84 | 3.66 |
| 622589 | 3,3'-[4-(1,3-benzodioxol-5-yl)-1,2,4-dithiazolidine-3,5-diylidene]bis[1,1-dimethyl(thiourea)] | 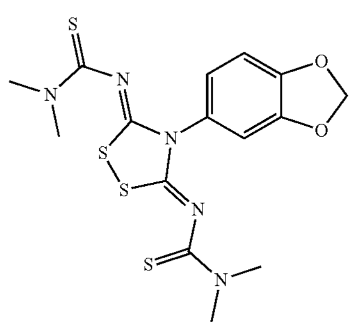 [SMILES: CN(C)C(=S)/N=c1\ss/c(=N\C(=S)N(C)C)n1-c1ccc2c(c1)OCO2] | 4.32 | 1.17 |
| 35542 | Xanthoxylin N | 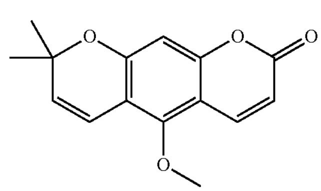 [SMILES: COc1c2c(cc3oc(=O)ccc13)OC(C)(C)C=C2] | 4.08 | 4.71 |

TABLE 2-continued

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 637993 | 5-{[2-(diethylamino)ethyl]amino}-8-methoxy-1-methyl-6h-imidazo[4,5,1-de]acridin-6-one hydrochloride (1:1) | 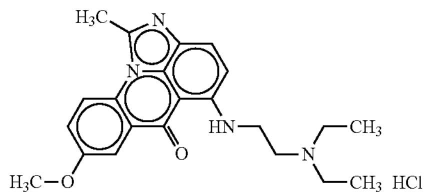 | 3.7 | 6.34 |
| 26040 | 1-Piperidineethanol, α-[p-(p-chlorostyryl)phenyl] | 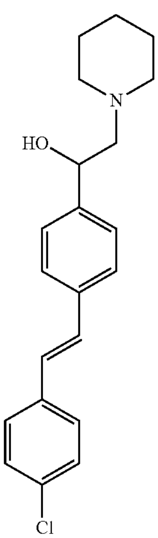 [SMILES: OC(CN1CCCCC1)c1ccc(/C=C/c2ccc(Cl)cc2)cc1] | 3.38 | 1.2 |
| 265211 | Rhodirubin E | 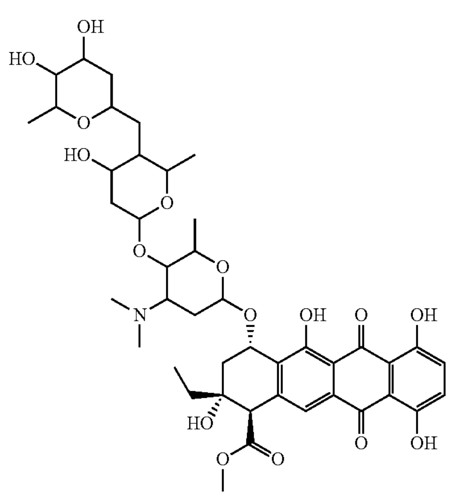 [SMILES: CC[C@@]1(O)C[C@H](OC2CC(N(C)C)C(OC3CC(O)C(CC4CC(O)C(O)C(C)O4)C(C)O3)C(C)O2)c2c(cc3c(c2O)C(=O)c2c(O)ccc(O)c2C3=O)[C@H]1C(=O)OC] | 3.36 | 1.47 |

TABLE 2-continued

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 641607 | 3-(2-(Hydroxyimino)-1,2-bis(4-methoxyphenyl)ethyl)-1-benzofuran-2(3H)-one | 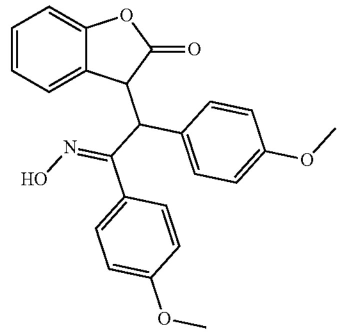 [SMILES: COc1ccc(/C(=N\O)C(c2ccc(OC)cc2)C2C(=O)Oc3ccccc32)cc1] | 3.25 | 1.27 |
| 335142 | 6H-Pyrido[4,3-b]carbazole-1-carboxamide, 5,11-dimethyl-, monohydrochloride (CaCx) | 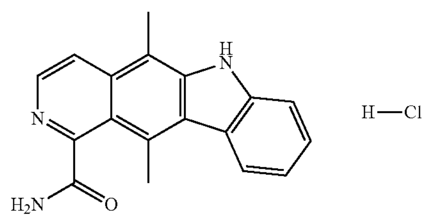 [SMILES: Cc1c2ccnc(C(N)=O)c2c(C)c2c1[nH]c1ccccc12 ; Cl] | 2.95 | 6.44 |
| 24048 | 2-(methyl(2-(2-pyridinyl)ethyl)amino)-9H-fluoren-9-one | 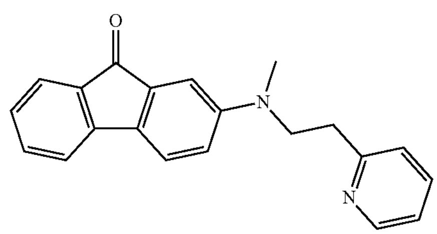 [SMILES: CN(CCc1ccccn1)c1ccc2c(c1)C(=O)c1ccccc1-2] | 2.84 | 1.62 |
| 293927 | (3E)-3-(5-phenyl-3H-1,2-dithiol-3-ylidene)-2H-chromene-2,4(3H)-dione | 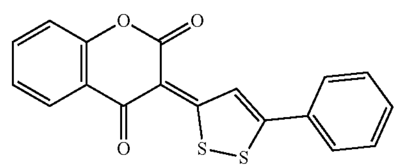 [SMILES: O=C1Oc2ccccc2C(=O)/C1=C1/C=C(c2ccccc2)SS1] | 2.82 | 1.77 |
| 642649 | 2-(1,3-Benzodioxol-5-yl)-1-(6-chloro-3-hydroxy-2-quinoxalinyl)-2-hydroxyethanone | 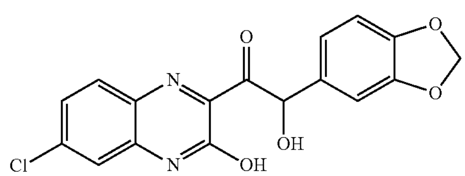 [SMILES: O=C(c1nc2ccc(Cl)cc2nc1O)C(O)c1ccc2c(c1)OCO2] | 2.8 | 0.85 |
| 623051 | 4-(1,3-Benzoxazol-2-yl)-1-(4-chloro-2-methylphenyl)-2,3,5,6-piperidinetetrone | 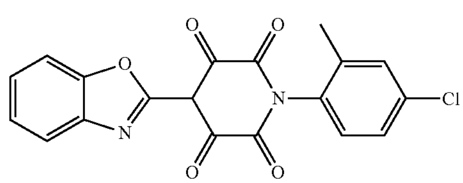 [SMILES: Cc1cc(Cl)ccc1N1C(=O)C(=O)C(c2nc3ccccc3o2)C(=O)C1=O] | 2.74 | 0.97 |
| 302358 | Piperidinium, 1-[4-(4-methoxyphenyl)-1,3-dithiol-2-ylidene]-, sulfate (1:1) | 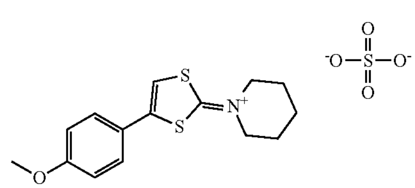 | 2.72 | 0.84 |

TABLE 2-continued

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 321803 | 4-Nitroestrone 3-methyl ether | 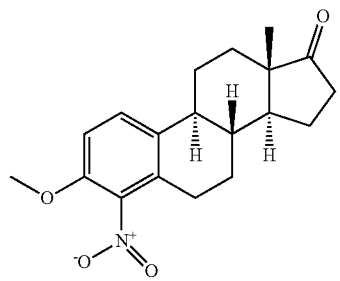 | 2.71 | ND |
| 643163 | 2-(3-Bromo-4-dimethylamino benzylidene)-1-indanone | 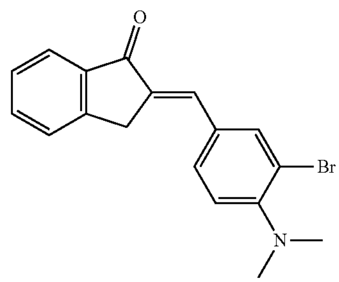 [SMILES: CN(C)c1ccc(/C=C2\Cc3ccccc3C2=O)cc1Br] | 2.64 | 0.79 |
| 681730 | 2,2'-(1,3-phenylenebis (methylene))bis(azanediyl)bis(2-phenylacetonitrile) | 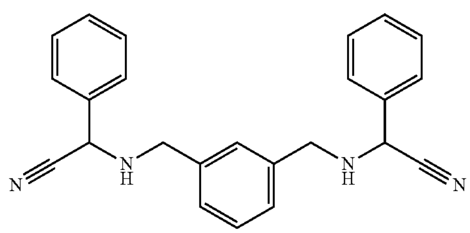 [SMILES: N#CC(NCc1cccc(CNC(C#N)c2ccccc2)c1)c1ccccc1] | 2.48 | 1.6 |
| 643175 | 2-(3,4-Dimethoxy benzylidene)-1-tetralone | 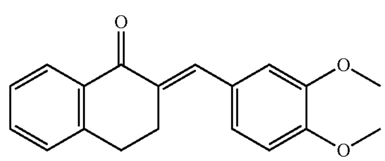 [SMILES: COc1ccc(/C=C2\CCc3ccccc3C2=O)cc1OC] | 2.47 | 0.89 |
| 337851 | Predorine | 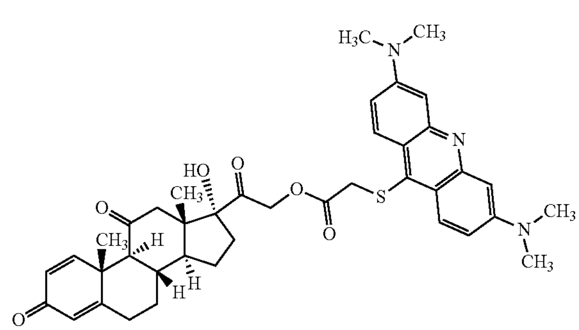 | 2.37 | 1.23 |

TABLE 2-continued

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 640637 | 3-Phenylacrylaldehyde N'-(5,6-diphenyl-1,2,4-triazin-3-yl)-N-phenylthiosemicarbazone | 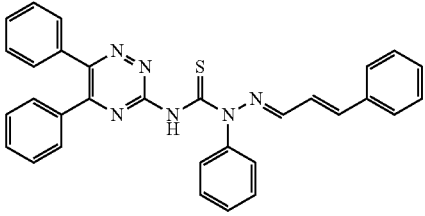 [SMILES: S=C(Nc1nnc(-c2ccccc2)c(-c2ccccc2)n1)N(/N=C/C=C/c1ccccc1)c1ccccc1] | 2.32 | 1.16 |
| 314622 | 5H-[1,3]Dioxolo[5,6]indeno[1,2-c]isoquinoline-5,12-dione, 2,3-dimethoxy-6-methyl- | 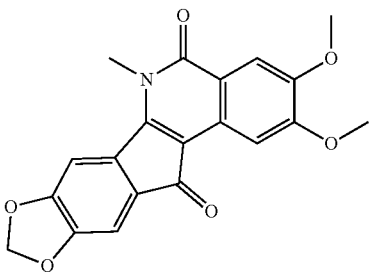 [SMILES: COc1cc2c3c(n(C)c(=O)c2cc1OC)-c1cc2c(cc1C3=O)OCO2] | 2.31 | 2.51 |
| 604535 | (2R)-1-[(2R)-2-methyl-3-phenylcarbonylsulfanyl-propanoyl]-2,3-dihydroindole-2-carboxylic acid | 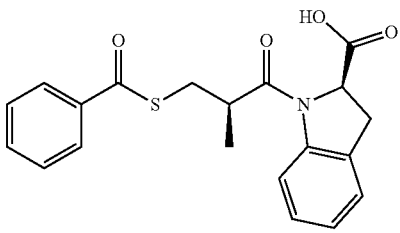 [SMILES: C[C@@H](CSC(=O)c1ccccc1)C(=O)N1c2ccccc2C[C@@H]1C(=O)O] | 2.26 | 1.07 |
| 163443 | 2-(5,11-dimethyl-6H-pyrido[4,3-b]carbazol-6-yl) ethyl benzoate | 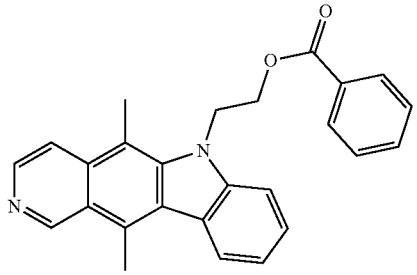 [SMILES: Cc1c2cnccc2c(C)c2c1c1ccccc1n2CCOC(=O)c1ccccc1] | 2.24 | 6.49 |
| 126771 | Dichlorolawsone | 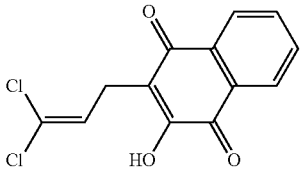 [SMILES: O=C1C(O)=C(CC=C(Cl)Cl)C(=O)c2ccccc21] | 2.23 | 3.27 |
| 643174 | 2-(3,4-Dimethoxybenzylidene)-1-indanone | 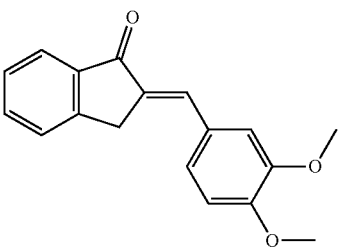 [SMILES: COc1ccc(/C=C2\Cc3ccccc3C2=O)cc1OC] | 2.17 | 1.29 |

TABLE 2-continued

Validation gene expression data

| Compound ID | Compound Name | Chemical Structure | SAMD9 expression fold change in HeLa reporter assay** | SAMD9 expression fold change in HeLa cells*** |
|---|---|---|---|---|
| 284751 | Adenosine, 8-chloro-, cyclic 3',5'-(hydrogen phosphate) | 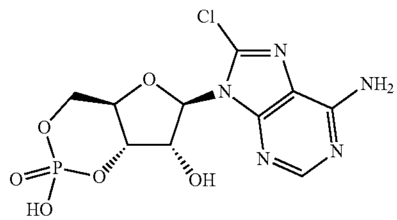 | 2.14 | 0.87 |
| 601101 | 2-(2-(2-(1,2-Benzisoxazol-3-yl)vinyl)phenoxy)-N,N-diethylethanamine hydrochloride | 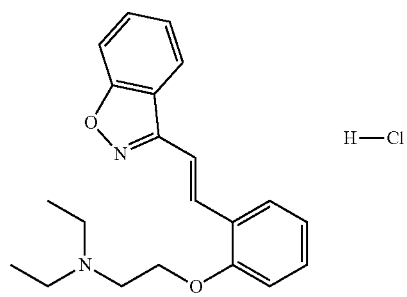 [SMILES: CCN(CC)CCOc1ccccc1/C=C/c1noc2ccccc12 ; Cl] | 2.13 | ND |
| 672425 | 1,2-Benzo-8-(L-alanyl)-3-phenoxazone nitrate salt | 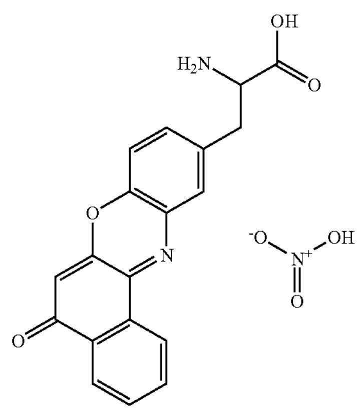 | 2.11 | 0.98 |
| 658350 | 2-(2-(2-(5-(Anilinomethylene)-3-ethyl-4-oxo-1,3-thiazolidin-2-ylidene)hydrazino)-1,3-thiazol-5-yl)-N-(2-methylphenyl)acetamide | 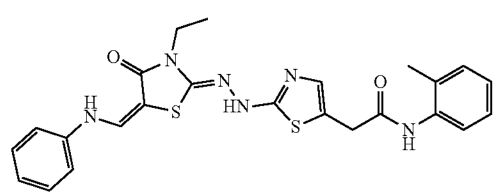 [SMILES: CCN1C(=O)/C(=C\Nc2ccccc2)S/C1=N\Nc1ncc(CC(=O)Nc2ccccc2C)s1] | 2.03 | 1.01 |
| 139109 | N-(3-methylphenyl)-3-(4-nitrophenyl)acrylamide | 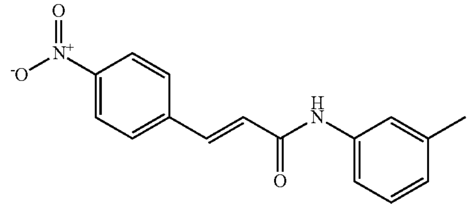 | 2.03 | 0.72 |

*ND: not determined
**Fold increase in promoter activity assessed by the luciferase assay as compared with cells treated with vehicle only
***Fold increase in RNA gene expression as compared with cells treated with vehicle only Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating skin inflammation in a subject in need thereof, the method comprising administering to the subject a therapeutically effective amount of a compound represented by Formula I:

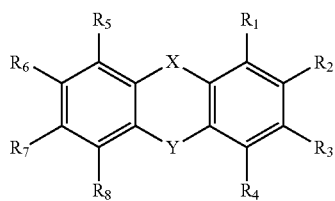

Formula I or a pharmaceutically acceptable salt thereof, wherein:
X is N—$R_9$ and $R_9$ is hydrogen or alkyl;
Y is absent;
$R_1$-$R_4$ are each independently hydrogen, alkyl, cycloalkyl, or trihaloalkyl;
$R_5$ and $R_8$ are each independently hydrogen, alkyl, cycloalkyl, or trihaloalkyl; and
$R_6$ and $R_7$ form together a -pyridine,
wherein each of said alkyl, cycloalkyl and pyridine is independently substituted or unsubstituted,
thereby treating the skin inflammation.

2. The method of claim 1, wherein the skin inflammation is selected from the group consisting of an atopic dermatitis, a contact dermatitis, a dermatitis herpetiformis, a generalized exfoliative dermatitis, a seborrheic dermatitis, a psoriasis, a drug rash, an erythema multiforme, an erythema nodosum, a granuloma annulare, a poison ivy, a poison oak, a toxic epidermal necrolysis, an acne and a rosacea.

3. The method of claim 1, wherein the skin inflammation is psoriasis.

4. The method of claim 1, wherein $R_1$-$R_4$ are each hydrogen.

5. The method of claim 1, wherein $R_5$ and $R_8$ are each independently an alkyl.

6. The method of claim 1, wherein:
$R_1$-$R_4$ and $R_9$ are each hydrogen; and
$R_5$ and $R_8$ are each an unsubstituted alkyl.

7. The method of claim 6, wherein $R_5$ and $R_8$ are each an unsubstituted methyl.

8. The method of claim 1, wherein said pyridine is substituted by an amide group.

9. The method of claim 7, wherein said pyridine is substituted by an amide group.

10. The method of claim 1, wherein the compounds is:

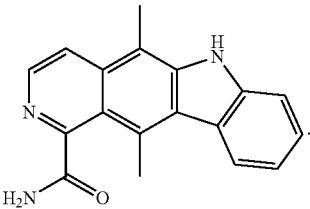

11. The method of claim 1, wherein the compound is:

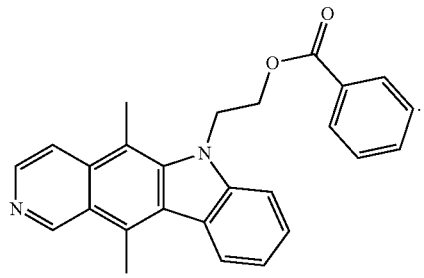 [SMILES: Cc1c2cnccc2c(C)c2c1c1ccccc1n2CCOC(=O)c1ccccc1]

* * * * *

```
                        SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 1
cgagcaaggt ccttccatag tg                                            22

<210> SEQ ID NO 2
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 2
ccgatgacct cacagctcaa g                                             21

<210> SEQ ID NO 3
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 3
gggcagtcga gtggtttgg                                                19

<210> SEQ ID NO 4
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 4
ttgccgacag gatgcagaag ga                                            22

<210> SEQ ID NO 5
<211> LENGTH: 585
<212> TYPE: DNA
<213> ORGANISM: Artificial Sequence
<220> FEATURE:
<223> OTHER INFORMATION: A DNA fragment spanning 585bp upstream to the
      SAMD9 predicted transcription start site (TSS)

<400> SEQUENCE: 5
cctgacactg accttagaaa agataaatct ctacaatgtg accatcaggt ctgctgcagc    60
cctggtctgc tctgcaataa atgaatttag cacttattgg ggtgctcaaa gaagtcctat   120
ccctgaaaga cattctttac actttaggaa aacaggaatg gacagtaact ccaccttaa    180 aggccagtga aatattgacc tagagtatct ccaacctggt gctctacaag gctgggactg   240
caatgtaaac tcatattccc aagggatcaa ttaagccaga atatcccaca gtttgtctat   300
```

```
aacaagacaa tggggctttc tgcagccctc aaaactctca agtgaggaaa aattgttaag    360
ccttcagatt ttaaccaagc agaccagaag gtggtatata gccatagctt attaaaaagc    420
atttcagata gaaaggcgg tgctgtaatt tcagatctga gaaatgaaac tgaaaccaaa    480
cctatattct tccttcccca acctcccagt tgttaaacac gccctgctgt ttctgagcca    540
attagagctt gctgtgagac agaagcagag aatacataga cttcc                   585
```